US011147902B2

(12) United States Patent
Lodhi et al.

(10) Patent No.: US 11,147,902 B2
(45) Date of Patent: *Oct. 19, 2021

(54) POLYMERIC COATINGS AND METHODS FOR CELL ATTACHMENT

(75) Inventors: Muhammad Lodhi, Eagan, MN (US); Tahmina Naqvi, Blaine, MN (US); Gary Oppermann, St. Louis Park, MN (US)

(73) Assignee: Surmodics, Inc., Eden Prairie, MN (US)

( * ) Notice: Subject to any disclaimer, the term of this patent is extended or adjusted under 35 U.S.C. 154(b) by 1702 days.

This patent is subject to a terminal disclaimer.

(21) Appl. No.: 11/490,414

(22) Filed: Jul. 20, 2006

(65) Prior Publication Data

US 2007/0032882 A1    Feb. 8, 2007

Related U.S. Application Data

(60) Provisional application No. 60/700,860, filed on Jul. 20, 2005.

(51) Int. Cl.
| A61L 27/34 | (2006.01) |
| A61L 27/38 | (2006.01) |
| A61L 27/40 | (2006.01) |
| A61L 31/10 | (2006.01) |
| A61L 31/12 | (2006.01) |

(52) U.S. Cl.
CPC ............. *A61L 27/34* (2013.01); *A61L 27/38* (2013.01); *A61L 27/40* (2013.01); *A61L 31/10* (2013.01); *A61L 31/12* (2013.01)

(58) Field of Classification Search
CPC ...................................................... A61L 27/34
See application file for complete search history.

(56) References Cited

U.S. PATENT DOCUMENTS

| 4,186,745 | A | * | 2/1980 | Lewis ................... A61L 29/041 604/265 |
| 5,002,582 | A | | 3/1991 | Guire et al. |
| 5,263,992 | A | | 11/1993 | Guire |
| 5,407,623 | A | * | 4/1995 | Zachariades ......... A61C 15/041 264/119 |
| 5,414,075 | A | | 5/1995 | Swan et al. |
| 5,512,474 | A | | 4/1996 | Clapper et al. |
| 5,563,056 | A | * | 10/1996 | Swan ............... A61K 47/48007 424/486 |
| 5,637,460 | A | | 6/1997 | Swan et al. |
| 5,714,360 | A | | 2/1998 | Swan et al. |
| 5,744,515 | A | | 4/1998 | Clapper |
| 5,834,556 | A | | 11/1998 | Desai et al. |
| 5,858,653 | A | * | 1/1999 | Duran et al. .................. 435/6.12 |
| 5,942,555 | A | | 8/1999 | Swanson et al. |
| 5,948,655 | A | | 9/1999 | Bader |
| 6,090,995 | A | | 7/2000 | Reich et al. |
| 6,121,027 | A | | 9/2000 | Clapper et al. |
| 6,548,299 | B1 | | 4/2003 | Pykett et al. |
| 6,656,517 | B2 | * | 12/2003 | Michal et al. ............... 427/2.24 |
| 7,550,444 | B2 | * | 6/2009 | Stucke et al. ..................... 514/56 |
| 2002/0004140 | A1 | * | 1/2002 | Swan ..................... A61L 29/085 428/500 |
| 2003/0165613 | A1 | * | 9/2003 | Chappa et al. ............... 427/2.24 |
| 2003/0181423 | A1 | * | 9/2003 | Clapper ................. A61L 27/14 514/100 |
| 2004/0044404 | A1 | * | 3/2004 | Stucke .................. A61L 29/085 623/1.46 |
| 2004/0258726 | A1 | * | 12/2004 | Stupp et al. ................... 424/423 |
| 2005/0095695 | A1 | | 5/2005 | Schindler et al. |
| 2005/0281857 | A1 | * | 12/2005 | Heyer et al. ................... 424/423 |
| 2006/0067908 | A1 | * | 3/2006 | Ding ....................... A61L 31/10 424/78.27 |
| 2007/0082393 | A1 | | 4/2007 | Lodhi et al. |

FOREIGN PATENT DOCUMENTS

| CA | 2615868 C | 4/2014 |
| EP | 0 402 718 | 12/1990 |
| EP | 1904118 A1 | 1/2018 |
| JP | 2009502243 A | 1/2009 |
| WO | WO 2003/074099 | 6/2003 |
| WO | WO 2007/012050 | 1/2007 |
| WO | WO 2007/012051 | 1/2007 |

OTHER PUBLICATIONS http://www.merriam-webster.com/dictionary/pendent.*
http://en.wikipedia.org/wiki/Polymer.*
http://en.wikipedia.org/wiki/Copolymer#Graft_copolymers.*
Fischer et al. (1999) Pharm. Res. 16, 1273-1279.
International Search Report for International Application No. PCT/US2006/028253, dated Dec. 22, 2006 (5 pgs).
International Search Report for International Application No. PCT/US2006/028252, dated May 1, 2007 (4 pgs).
Makohliso, et al., "Application of Teflon-AF® thin films for bio-patterning of neural cell adhesion," Biosensor & Bioelectronics, 13, 1998, pp. 1227-1235.
Hu, et al., "Polyethyleneimine Functionalized Single-Walled Carbon Nanotubes as a Substrate for Neuronal Growth," The Journal of Physical Chemistry Letters, 109, 2005, pp. 4285-4289.
Hu, et al., "Chemically Functionalized Carbon Nanotubes as Substrates for Neuronal Growth," Nano Letters, vol. 4, No. 3, 2004, pp. 507-511.
Bledi, et al., "Culturing neuronal cells on surfaces coated by a novel polyethyleneimine-based polymer," Brain Research Protocols, 5, 2000, pp. 282-289.

(Continued)

*Primary Examiner* — Sarah Alawadi
(74) *Attorney, Agent, or Firm* — Kagan Binder, PLLC

(57) ABSTRACT

The invention provides cell-adherent polymeric coatings for articles, the coating including a synthetic, non-biodegradable polymer having a plurality of pendent amine groups, wherein the polymer is covalently immobilized on the article via latent reactive groups. The invention also provides methods for the long-term attachment of cells using the polymeric coatings.

6 Claims, 13 Drawing Sheets
Specification includes a Sequence Listing.

(56) References Cited

OTHER PUBLICATIONS

Qian, et al., "Improving the expansion and neuronal differentiation of mesenchymal stem cells through culture surface modification," Biomaterials, 25, 2004, pp. 1331-1337.

Ahlemeyer, et al., "Staurosporine-induced apoptosis in cultured chick embryonic neurons is reduced by polyethylenimine of low molecular weight used as a coating substrate," Neuroscience Research, 37, 2000, pp. 245-253.

Deligianni, et al., "Effect of surface roughness of hydroxyapatite on human bone marrow cell adhesion, proliferation, differentiation and detachment strength," Biomaterials, 22, 2001, pp. 87-96.

Vancha, et al., "Use of polyethyleneimine polymer in cell culture as attachment factor and lipofection enhancer," BMC Biotechnology, vol. 4, No. 23, 2004, 12 pgs.

Keselowsky, et al., "Surface chemistry modulates focal adhesion composition and signaling through changes in integrin binding," Biomaterials, 25, 2004, pp. 5947-5954.

Chim, et al., "Efficacy of glow discharge gas plasma treatment as a surface modification process for three-dimensional poly $_{(D,L)}$-lactide) scaffolds," Journal of Biomedical Materials Research, 2003-65A, pp. 327-335.

Lan, et al., "Myoblast proliferation and differentiation on fibronectin-coated self assembled monolayers presenting different surface chemistries," Biomaterials, 26, 2005, pp. 4523-4531.

Bain, et al., "Tissue-culture surfaces with mixtures of aminated and fluorinated functional groups. Part 1. Synthesis and characterization," J. Biomater. Sci. Polymer Edn, vol. 14, No. 4, 2003, pp. 325-339.

Vleggeert-Lankamp, et al., "Adhesion and proliferation of human Schwann cells on adhesive coatings," Biomaterials, 25, 2004, pp. 2741-2751.

Young, et al., "Covalent bonding of lysine to EVAL membrane surface to improve survival of cultured cerebellar granule neurons," Biomaterials, 24, 2003, pp. 1477-1486.

Ruardij, et al., "Adhesion and Patterning of Cortical Neurons on Polyethylenimine- and Fluorocarbon-Coated Surfaces," IEEE Transaction on Biomedical Engineering, vol. 47, No. 12, Dec. 2000, pp. 1593-1599.

Miller, et al., "Endothelial and vascular smooth muscle cell function on poly(lactic-co-glycolic acid) with nano-structured surface features," Biomaterials, 25, 2004, pp. 53-61.

Wang, et al., "Attachment, proliferation and differentiation of osteoblasts on random biopolyester poly(3-hydroxybutyrate-co-3-hydroxyhexanoate) scaffolds," Biomaterials, 25, 2004, pp. 669-675.

Rosa, et al., "Osteoblastic differentiation of cultured rat bone marrow cells on hydroxyapatite with different surface topography," Dental Materials, 19, 2003, pp. 768-772.

Andrzejewska, et al., "Effect of polyacid aqueous solutions on photocuring of polymerizable components of resin-modified glass ionomer cements," Dental Materials, 19, 2003, pp. 501-509.

Engstrom, et al., "The Effect of Hyaluronan on Bone and Soft Tissue and Immune Response in Wound Healing," J. Periodontol, vol. 72, No. 9, Sep. 2001, pp. 1192-1200.

* cited by examiner

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 1

Arg Gly Asp Ser
1

<210> SEQ ID NO 2
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 2

Arg Glu Asp Val
1

<210> SEQ ID NO 3
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 3
```

Arg Gly Asp Val
1

<210> SEQ ID NO 4
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 4

Leu Arg Gly Asp Asn
1               5

<210> SEQ ID NO 5
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 5

Ile Lys Val Ala Val
1               5

<210> SEQ ID NO 6
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 6

Tyr Ile Gly Ser Arg
1               5

<210> SEQ ID NO 7
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 7

Pro Asp Ser Gly Arg
1               5

<210> SEQ ID NO 8
<211> LENGTH: 10
<212> TYPE: PRT
<213> ORGANISM: Artificial Sequence
<220> FEATURE:
<223> OTHER INFORMATION: chemically synthesized peptide

<400> SEQUENCE: 8

Arg Asn Ile Ala Glu Ile Ile Lys Asp Ala
1               5                   10

<210> SEQ ID NO 9
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 9

Arg Gly Asp Thr

```
<210> SEQ ID NO 10
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 10

Asp Gly Glu Ala
1

<210> SEQ ID NO 11
<211> LENGTH: 15
<212> TYPE: PRT
<213> ORGANISM: Artificial Sequence
<220> FEATURE:
<223> OTHER INFORMATION: chemically synthesized peptide

<400> SEQUENCE: 11

Gly Thr Pro Gly Pro Gln Gly Ile Ala Gly Gln Arg Gly Val Val
1               5                   10                  15

<210> SEQ ID NO 12
<211> LENGTH: 11
<212> TYPE: PRT
<213> ORGANISM: Artificial Sequence
<220> FEATURE:
<223> OTHER INFORMATION: chemically synthesized peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Val Thr Xaa Gly Phe Tyr Val Val Met Trp Lys
1               5                   10
```

POLYMERIC COATINGS AND METHODS FOR CELL ATTACHMENT

CROSS-REFERENCE TO RELATED APPLICATION

The present non-provisional Application claims the benefit of U.S. Provisional Application having Ser. No. 60/700,860, filed on Jul. 20, 2005, and entitled, "Polymeric Coatings and Methods for Cell Maintenance and Differentiation." Also, the entire contents of the ASCII text file entitled "SRM0063US_Sequence_Listing.txt" created on Jan. 30, 2017, having a size of 3 kilobytes is incorporated herein by reference.

FIELD OF THE INVENTION

The invention relates to coatings that include a non-biodegradable amine-presenting polymer and methods for promoting the adherence of cells on surfaces that include these coatings. The invention also relates to methods of differentiating cells, as well as methods for maintaining cells on surfaces having these coatings.

BACKGROUND OF THE INVENTION

Various approaches have been used to provide surfaces that are suitable for cell attachment and growth. Many cells are anchorage dependent, meaning that they must demonstrate some type of attachment to a substrate in order to proliferate or differentiate. In vivo, cells can attach to protein factors present in the basement membrane, which is a structure that supports an overlying epithelium or endothelium. The basement membrane consists of a membrane called the basal lamina and an underlying network of collagen fibrils. Due to its capability to provide an excellent substrate for cell attachment and growth, artificial surfaces for cell attachment based on components found in basement membranes have been fabricated. Such artificial surfaces have been used in vivo, such as in implantable medical devices, and in vitro, such as in cell culture articles.

Charged surfaces have been used to promote the attachment of cells to a substratum. However, not all charged surfaces are suitable for the sufficient attachment of cells during culturing processes. For example, some negatively charged surfaces do not provide a suitable substrate because many cells do not display a sufficient amount of positively charged proteins to mediate cell attachment to the surfaces.

Natural polypeptide-based cell attachment factors such as collagen, fibronectin, and laminin have been used to enhance the attachment of cells to a substrate. Biodegradable synthetic polymeric cations such as polylysine and polyornithine have also been used to provide coatings that promote the attachment of various anchorage dependent cell types. One problem with the use of these types of polymeric materials is that they can degrade over a period of time by proteases which may become present in the liquid medium of a culture, or that are present in vivo in serum. Therefore, surfaces containing these materials may only be useful for cell attachment for a limited period of time. Properties related to cell adhesion may be compromised by the degradation of the materials present within the coating.

Furthermore, some coatings that are used to promote cell attachment may also be problematic from the standpoint that coating materials may be lost from the coating if not properly attached to the surface of the article. These materials may then become present in the liquid media or body fluid and affect cells that come in contact with it. For example, polymeric materials lost from the coating may bind the surface of the cells and affect cell attachment to the substrate or may affect cell-cell interactions in culture. Some polymeric materials may also be detrimental to cell viability.

Therefore, there is a need to provide improved polymeric coatings for articles used in processes involving culturing cells. Such improved coatings could provide for useful cell culture articles that would benefit processes involving the maintenance and differentiation of primary cells, cells lines that are difficult to culture, and stem cells. Such coatings could also be used to coat the surfaces of implantable medical articles for in vivo use. Accordingly, this would benefit the technology of tissue specific regeneration for the treatment of a wide array of diseases and conditions.

SUMMARY OF THE INVENTION

In one aspect, the present invention provides coatings for cell culture articles that are useful in methods for culturing cells, and, in particular, methods for keeping cells in culture for a protracted period of time (long term cultures). Culturing, as used herein, refers to processes involving placing metabolically active cells in a cell culture article having a polymeric coating as described herein. The polymeric coatings of the present invention have been shown to provide an ideal surface for long-term cell culture because of their stability, their ability to provide an excellent surface for cell attachment, and their ability to be used to culture a wide variety of cell types.

In conjunction with the coatings, the cells are cultured in a liquid medium to provide a desired metabolically active state. The coatings can be used to promote one or more metabolically active cellular states, including states wherein the cell is quiescent (a non-proliferative and non-differentiating state), states of cell proliferation, and states of cell differentiation.

In another aspect of the invention, the coatings are provided on an implantable medical device. In some ways, similar to the function of the coatings as provided in vitro, the coatings can be used on the surface of a medical article to promote cell attachment. This is useful for a number of applications, including promotion of tissue formation, epithelialization, and angiogenesis.

The inventive coatings include a non-biodegradable polymer having pendent amine groups, wherein the coating also includes one or more latent reactive groups. The latent reactive groups are used to covalently bind the polymer to the surface of an article, such as a part of a cell culture device or apparatus, or a part of an implantable medical device. The latent reactive groups may be provided on the polymer as pendent latent reactive groups. Alternatively, pendent latent reactive groups may be included on a compound independent of the polymer and then used to couple the polymer to the substrate surface.

It is believed that the binding via the pendent latent reactive groups provides a coating wherein the polymer is optimally configured on the surface to promote cell adhesion. In some aspects, the pendent latent reactive group is a photoreactive group. Given this, the coatings of the present invention can generally be used in a method for cell attachment, wherein the cells can remain attached to the surface for a protracted period of time.

In some aspects of the invention, the polymer of the present invention includes a pendent amine-containing group of the following formula:

—$R_1R_2NR_3R_4$ wherein $R_1$ is:

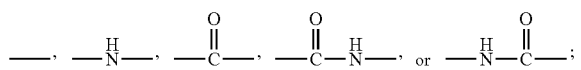

wherein $R_2$ is $C_1$-$C_8$ linear or branched alkyl; and
wherein $R_3$ and $R_4$ are individually H or $C_1$-$C_6$ linear or branched alkyl.

In some aspects, $R_1$ is

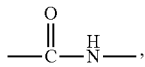

$R_2$ is $C_2$-$C_4$ linear or branched alkyl; and $R_3$ and $R_4$ are individually H or $CH_3$.

Exemplary amine containing groups include those found on polymerizable monomers such as 3-aminopropylmethacrylamide (APMA), 3-aminoethylmethacrylamide (AEMA), and dimethylaminopropylmethacrylamide (DMAPMA). In some aspects, polymers including pendent amine groups and latent reactive groups can be formed by copolymerizing a monomer having a group —$R_1R_2NR_3R_4$ as defined above with a comonomer bearing a latent reactive group. In other aspects, a polymer can be formed by polymerizing a monomer having the formula $R_1R_2NR_3R_4$ and then reacting one or more pendent amine groups with a compound having a latent reactive group.

In other aspects, the polymer having pendent amine groups is selected from polyethyleneimine (PEI), polypropyleneimine (PPI), and polyamidoamine. PEI can be formed by the polymerization of ethylene imine; optionally a monomer having a polymerizable group and a latent reactive group can be copolymerized with ethylene imine to form PEI having pendent latent reactive groups. In one specific aspect the polymer includes polyethyleneimine with one or more latent photoreactive group(s).

Latent reactive groups refer to groups that respond to specific applied external stimuli to undergo active specie generation with resultant covalent bonding to a target. The latent reactive groups generate active species such as free radicals, nitrenes, carbenes, and excited states of ketones upon absorption of external electromagnetic or kinetic (thermal) energy. In one aspect, the latent reactive group is a photoreactive group that can be activated to an active state to provide bonding between the polymer and the surface of a cell culture article. Exemplary photoreactive groups include aryl ketones, such as acetophenone, benzophenone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives.

A polymer having pendent amine and one or more latent reactive groups can be coupled to, or formed on the surface of an article using any suitable method. One method includes disposing a pre-formed polymer on the surface and then activating the latent reactive groups to bind the polymer to the surface. In these cases the latent reactive groups can be pendent or independent of the polymer. Alternatively monomeric material can be polymerized on the surface to form a polymer having pendent amine and one or more latent reactive groups that couple the polymer to the surface.

The polymeric coatings of the present invention have been shown to be useful for the preparation of various cell culture articles. In some aspects, the cell culture article is a two-dimensional cell culture article, which refers to articles having a coated surface wherein cells grow in a single plane on the two-dimensional surface. Such two-dimensional cell culture articles include those such as wells of multi-well cell culture plates, cell culture dishes, and cell culture bottles. In other aspects, the cell culture article is a three-dimensional cell culture article, referring to articles having coated surfaces wherein cells grow in more than one plane on the article. The coated surfaces of three-dimensional cell culture articles can resemble scaffoldings on to which cells can attach. Such articles can be made from micro- or nano-structured materials, such as those formed from polymeric materials that have been treated to create surface topography, synthetic or natural micro- or nano-porous materials, including those formed from fibers.

The polymer having pendent amine groups is able to promote excellent adherence of cells during the culture process. This allows cells that display some degree of anchorage dependency to attach to the coating and exhibit one or more metabolic activities depending on the type of cell that is cultured and the type of media that the cell is cultured in. The coatings are therefore particularly useful for culturing cells that are non-adherent, poorly adherent, or moderately adherent. The inventive coatings are also particularly useful for providing coatings that allow cell proliferation and differentiation.

The invention provides coatings that are remarkably stable and effective for cell culturing processes. Accordingly, the coatings of the present invention are particularly useful for procedures involving long term culturing of cells.

In these aspects, it has been found that the present coatings are particularly advantageous, as the amine-presenting polymer does not degrade in the presence of the culture medium and therefore can be used to promote the adherence of cells in culture for a considerable period of time. This is in comparison to coatings that are primarily composed of degradable natural polymers such as polypeptides and polysaccharides, as well as biodegradable synthetic polymers. These types of biodegradable coatings may degrade over a shorter period of time (such as a couple of weeks) and loose their ability to promote the adherence of cells in culture.

In addition, since the polymers of the present invention are covalently bonded to the surface of the culture article, there is minimal or no loss of the amine-presenting polymer from the surface. This is advantageous in many regards; first, since over the culture period, the potential for the cells to become or remain attached to the surface will not change. That is, the amount of amine-presenting polymer attached to the surface will not significantly change over time. Second, there is minimal risk of loss of the amine-presenting polymer into the culture. This is also advantageous, because polymer lost in the culture may otherwise change the properties of the cells. For example, the cells may become non-adherent, or may lose other properties conveyed by proteins on the surface of the cells. In addition, in some cases, polymer lost from the coating into the media may have a toxic effect on the cells. For example, toxic effects have reported for some polyethyleneimines having a molecular weight of 25 kDa and greater in different culture systems when the PEI was added extracellularly (Fischer et al. (1998) Eur. J. Cell Biol. 48, 108; Fischer et al. (1999) Pharm. Res. 16, 1723-1729). Therefore, the polymeric coatings of the present invention overcome some of the shortcomings found in coatings that have been traditionally used to promote cell attachment and culturing in the prior art.

Although the present coatings are based on a non-biodegradable amine-presenting polymer, other non-biodegradable or degradable materials, such as biodegradable polymers may be present in the coating. For example, while biodegradable polymers may be present in the coating and provide an advantage for culturing cells for a shorter time period, the non-biodegradable polymer remains present in the coating and provides an adherent surface during protracted periods of culturing.

In some aspects, the invention provides a method for the long term culturing of cells. The method includes the step of obtaining a cell culture article having a coating that includes a non-biodegradable synthetic polymer having a plurality of amine groups and latent reactive groups that couple the polymer to the surface of the article. The method further includes the step of disposing cells on the surface in an environment (liquid medium). Following the step of disposing, the cells are able to adhere to the coating, so the cells can maintain or be induced to have a desired physiological state. The method then includes the step of culturing the cells in a liquid medium for a protracted period of time. A protracted period of time generally refers to a period of time that is greater than 14 days. When indicated, the protracted period of time may be greater than 21 days, greater than 28 days, greater than 35 days, greater than 42 days, greater than 49 days, or greater than 56 days. In some aspects, therefore, the cells also may be kept in culture for a time period in the range of about 14 to about 60 days. A distinct advantage of the invention is that the cells do not have to be transferred to a new culture article having a fresh coating capable of promoting cell adherence. However, during the period of long term culturing, the liquid media can be changed, such as by replacement or by supplementation, to provide an environment that is suitable to achieve the desired physiological state.

In some aspects, over a period of the culturing process, the method can be used to maintain cells in a state of low metabolic activity (for example, maintaining quiescent cells). That is, in some aspects, cells can be maintained on the coated surfaces in an appropriate media without promoting a metabolic change in the cells, such as one that may change the morphology of the cells. This method can also be useful for maintaining cells, and can include expanding the population of cells by cell proliferation. Exemplary cell types that can be maintained in cell culture using the polymeric coatings of the present invention include undifferentiated cells, such as stem cells, or partially or fully differentiated cell types, such hepatocytes, islet cells, neurons, and astrocytes. The undifferentiated cells can include multipotent, totipotent, or pluripotent cell types.

In this regard, the coatings are particularly useful in that they provide coated articles that can be used for long-term maintenance of cells without a need to replace the coated article over a period of time.

In other aspects, over a period of the culturing process, the method can be used to promote the differentiation of cells. Any suitable pre-differentiated or progenitor cell type can be used. The method can include the steps of obtaining a coated surface and then disposing pre-differentiated cells on the coated surface, wherein the cells adhere to the coating. The method also includes a step of culturing the cells in the presence of an environment (liquid medium) that includes a component that can change the metabolic activity of the cells, leading to a change in one or more cellular aspects, such as cell morphology. The component can be a differentiation factor, which refers to any sort of component that promotes the maturation of the pre-differentiated cells into a partially or fully differentiated state. The method then includes the step of differentiating the cells that are in contact with the coated surface for a protracted period of time. When indicated, the protracted period of time may be greater than 14 days, greater than 21 days, greater than 28 days, greater than 35 days, greater than 42 days, greater than 49 days, or greater than 56 days. In some aspects, the cells also may be kept in culture for a time period in the range of about 14 to about 60 days, depending on the initial seeding density of the cells. During the period of long term culturing, the liquid media can be changed, such as by replacement or by supplementation, to provide an environment that is suitable to achieve the desired physiological state.

Exemplary cell types that can be differentiated according to the present invention include primary cells, neural precursors, bone marrow cells, stem cells, such as embryonic (blastocyst derived) stem cells, and the like.

In some aspects, the method is used to promote the maturation of neural precursor cells into a desired differentiated neuronal cell type. The polymeric coatings of the present invention have been shown to promote the attachment of neural precursor cells, which can then be cultured for a protracted period of time in the presence of one or more desired differentiation factors. The present coatings have been shown to promote neurite outgrowth and/or elongation, whereas neural precursors cultured on traditionally coated articles under the same media conditions did not survive. The present coatings also promoted the appearance of mature neuronal markers in a subset of neuronal cells growing on the coated substrates. The present coatings have also been shown to promote the formation of neural precursors into astrocytes.

DETAILED DESCRIPTION

Figure 1:
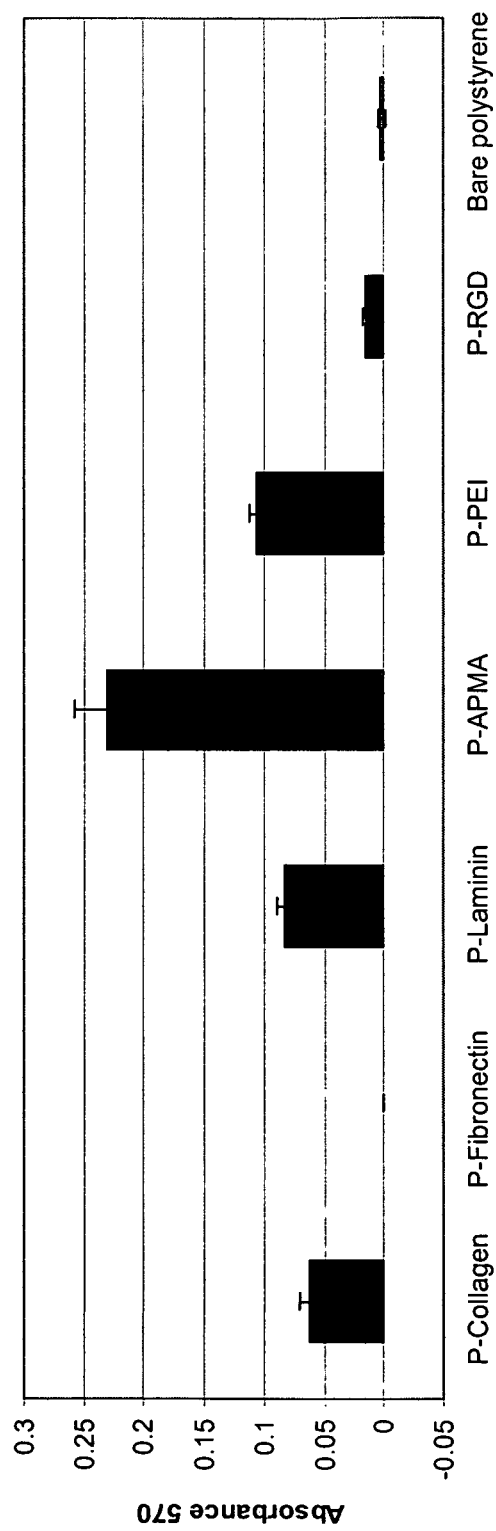
FIG. 1 is a graph showing the results of PC12 cell attachment on various photo-polymer coated and uncoated flat surfaces.

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

In some aspects, the present invention provides reagents and methods for providing a coating to the surface of a cell culture article, the coating including a polymeric material having a plurality of pendent amine groups and at least one latent reactive group that is used to couple the polymer to the surface of the cell culture article.

The polymeric coatings of the present invention can be formed on any type of cell culture article. However, in some aspects it is desirable to provide a cell culture article that provides a surface sufficient for the growth and differentiation of cells. Such an article ideally has a surface that supports the morphology of the differentiating cells. For example, in the case of differentiation of neural precursors, the surface allows the formation of neurites or other features of neural cells which are greater than 10 Jim, or greater than 200 µm.

Exemplary cell culture articles for two-dimensional cell culturing include, but are not limited to, multi-well plates, including 6 well and 12 well culture plates, and well as smaller welled culture plates such as 96, 384, and 1536 well plates, culture jars, culture dishes, culture flasks, culture plates, culture roller bottles, culture slides, culture tubes, and petri dishes.

The coatings of the present invention can also be formed on three-dimensional cell culture articles, which allow cells to grow in more than one plane on the article. The coated surfaces of three-dimensional cell culture articles can resemble scaffoldings on which cells can attach. Such articles can be made from micro- or nano-structured materials, such as those formed from polymeric materials that have been treated to create surface topography, synthetic or natural micro- or nano-porous materials, including those formed from fibers, including polyamid fibers. Exemplary three dimensional cell culture articles include multi-walled carbon nanotubes (MWCN; see Chen et al. (1998) *Science* 282:95); hydroxyapatite particulate surfaces (Rosa et al. (2003) Dental Mater. 19:768-772). The polymeric coatings can also be formed over the surface of natural materials, such as self-assembling peptide nanofiber scaffolds (Genove et al. (2005) Biomaterials. 26:3341-3351) and collagen/hyaluronic acid polyelectrolyte multilayers (Zheng et al. (2005) Biomaterials, 26:3353-61). In other cases, the three-dimension surface can be created from stabilized layers of microparticles.

The polymeric coatings can be formed on cell culture article which can be fabricated from a wide variety of materials. The materials used to form the structure of the cell culture article are referred to herein as "article materials" or "device materials" whereas the materials used to form the polymeric coatings herein referred to as "coating materials."

Example of materials which can be used to form the article onto which the coating can be formed include synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, and styrene.

Exemplary polymeric materials commonly used in cell culture articles include polystyrene and polypropylene.

Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketone.

Biodegradable polymers may also be used as article materials. Examples of classes of synthetic polymers that have been studied as biodegradable materials include polyesters, polyamides, polyurethanes, polyorthoesters, polycaprolactone (PCL), polyiminocarbonates, aliphatic carbonates, polyphosphazenes, polyanhydrides, and copolymers thereof. Specific examples of biodegradable materials that can be used in connection with implantable medical devices include polylactide, polygylcolide, polydioxanone, poly(lactide-co-glycolide), poly(glycolide-co-polydioxanone), polyanhydrides, poly(glycolide-co-trimethylene carbonate), and poly(glycolide-co-caprolactone). Blends of these polymers with other biodegradable polymers can also be used.

The polymeric coating of the present invention can also be formed on the surface of an article that is precoated with a different polymeric material. For example, articles can be pre-coated with Parylene or an organosilane material to provide a base coat onto which the amine-containing polymer can be disposed on and reacted with. Exemplary materials include metals, metal alloys, and ceramics. The metals and metal alloys include, but are not limited to, titanium, Nitinol, stainless steel, tantalum, and cobalt chromium. A second class of metals includes the noble metals such as gold, silver, copper, and platinum uridium. The ceramics include, but are not limited to, silicon nitride, silicon carbide, zirconia, and alumina, as well as glass, silica, and sapphire. Combinations of ceramics and metals are another class of biomaterials.

In other aspects of the invention, the polymeric coating is formed on the surface of an implantable medical article. The implantable medical article can be fabricated from any of the materials as described herein and suitable for use in the body. Exemplary medical articles include vascular implants and grafts, grafts, surgical devices; synthetic prostheses;

vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parental feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; birth control devices; breast implants; cardiac sensors; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects the medical article is associated with a fabric or fiber surface onto which the polymeric coating can be formed. Exemplary fabrics and fibers can be formed from polyesters, polypropylenes, polyethylenes, polyurethanes, polytetrafluoroethylenes, and polyamids. Polyethylene terephthalate (PET) is a commonly used polymer in fabrics. Blends of these polymers can also be utilized in the preparation of fibers, such as monofilament or multi-filament fibers, for the construction of fabrics. Commonly used fabrics include those such as nylon, velour, and DACRON™.

The coating can be used in a method to promote the attachment of cells to the surface of the coated article in vivo. Since the polymeric coatings provide long-term attachment of cells, the coatings of the present invention are particularly suitable for long-term implantable devices, such as those that reside in the body for a period of time of a month or longer. In some cases, the coatings may be used for the attachment of endothelial cells to the device surface and the stable formation of an endothelial layer of cells.

In some aspects, the inventive coatings include a non-biodegradable polymer having a plurality of pendent amine groups and also one or more pendent latent reactive groups. "Non-biodegradable" refers to polymers that are generally not able to be non-enzymatically, hydrolytically or enzymatically degraded. For example, the non-biodegradable polymer is resistant to degradation that may be caused by proteases. However, it is noted that while the coating includes a non-biodegradable amine-presenting polymer, the coating is not limited to non-biodegradable materials, and therefore may also include biodegradable materials, such as natural or synthetic biodegradable polymers.

The coating includes latent reactive groups wherein at least a portion of the groups are activated during the coating process to bond the polymer to the surface of the device. Therefore, in the formed coating, the groups which have undergone activation and bonding to a target moiety may also be referred to as "reacted groups."

By binding to the surface via the latent reactive groups, the immobilized polymer provides positively-charged amine groups to the surface of the article. It is thought that this binding arrangement allows for the formation of a very durable and effective surface for cell attachment. This surface has been shown to be highly effective for processes including maintenance and differentiation of cells on the coated article.

The plurality of pendent amine groups on the non-biodegradable polymer can provide a positive charge to the coating in pH conditions suitable for cell culture. For example, the non-biodegradable polymer provides a positive charge in conditions ranging from about pH 6.0 to about pH 8.0.

The non-biodegradable polymer can have primary amine, secondary amine, tertiary amine, or combinations of these amine groups pendent from the polymer.

In one aspect of the invention, an exemplary amine-containing group has the following formula: $R_1R_2NR_3R_4$, wherein $R_1$ is:

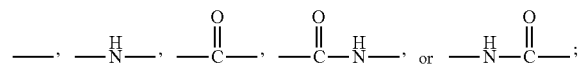

wherein $R_2$ is $C_1$-$C_8$ linear or branched alkyl; and wherein $R_3$ and $R_4$ are individually H or $C_1$-$C_6$ linear or branched alkyl. As pendent from the polymer, the amine-containing group can be represented by the formula $P$-$[R_1R_2NR_3R_4]$, P being a portion of the polymeric backbone.

In some more specific aspects, $R_1$ is

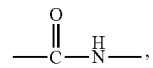

$R_2$ is $C_2$-$C_4$ linear or branched alkyl; and, $R_3$ and $R_4$ are individually H or $CH_3$.

Exemplary amine containing groups include those found on polymerizable monomers such as 3-aminopropylmethacrylamide (APMA), 3-aminoethylmethacrylamide (AEMA), dimethylaminopropylmethacrylamide (DMAPMA), and the like. Therefore, in some aspects, polymers including pendent amine groups and latent reactive groups can be formed by copolymerizing a monomer having a group —$R_1R_2NR_3R_4$ as defined above with a comonomer bearing a latent reactive group. Optionally, other non-amine or non-latent reactive group-containing monomers can be included in the polymer.

In one aspect, the polymer is formed by using an amine-containing monomer in a molar amount of about 10% or greater. In some aspects, the amine-containing monomer is present in an amount of 50% or greater, 60% or greater, 70% or greater, 80% or greater, 90% or greater, or 95% or greater. In another aspect, the monomer including the latent reactive group is present in an amount of up to about 10%, or an amount of about 5%. In some aspects the polymer includes amine-containing monomers in an amount in the range of about 90%-99.95%, and an amount of monomer including the latent reactive group in the range of about 10%-0.05%. An exemplary preparation of a copolymer includes about 98.4% amine-containing monomer, such as APMA, AEMA, or DMAPMA, and about 1.6% of monomer including the latent reactive group.

Defined control over amount of amine group and amount of latent reactive group can be exercised by copolymerizing an amine-containing monomer with a latent reactive group-containing monomer (and optionally a non-amine or non-photo reactive group-containing monomer). Other exemplary amine-containing polymers can be formed by the copolymerization of, for example, amine-containing monomers such as N-(2-amino-2-methylpropyl)methacrylamide, p-aminostyrene, allyl amine, or combinations thereof with a monomer having a pendent latent reactive groups to provide a polymer having pendent amine groups and latent reactive groups. These amine-containing monomers can also be copolymerized with other non-primary amine-containing monomers, such as acrylamide, methacrylamide, vinyl pyrrolidinone, or derivatives thereof, to provide a polymer having desired properties, such as a desired density of amine groups and photoreactive groups. Other suitable polymers that have amine groups include polymers that are formed from monomers such as 2-aminomethylmethacrylate, 3-(aminopropyl)-methacrylamide, and diallylamine. Dendrimers that include photogroups and pendent amine groups can also be used.

In some aspects a polymer having pendent amine groups and hydrophobic properties can be prepared. This can be achieved by one or more schemes for the synthesis of the polymer. For example, a polymer can be formed with a desired amount of hydrophobic monomers, such as (alkyl) acrylate monomers, or the amine-presenting monomers can include longer alkyl chain lengths. For example, any one or more of the groups $R_2$, $R_3$, and/or $R_4$ can include alkyl groups of 3 or more carbon atoms.

Another method for preparing the non-biodegradable polymer includes steps of derivatizing a preformed polymer with a compound that includes a latent reactive group. For example, a homopolymer or heteropolymer having pendent amine groups can be readily derivatized with a photoreactive group by reacting a portion of the pendent amine groups with a compound having a photoreactive group and a group that is reactive with an amine group, such as 4-benzoylbenzoyl chloride.

In some aspects, the polymer having pendent amine groups and at least one latent reactive group is selected from polyethyleneimine, polypropyleneimine, and polyamidoamine. In one specific aspect the polymeric material includes polyethyleneimine with one or more latent reactive group(s).

Latent reactive groups, broadly defined, are groups that respond to specific applied external stimuli to undergo active specie generation with resultant covalent bonding to a target. Latent reactive groups are those groups of atoms in a molecule that retain their covalent bonds unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups may be chosen to be responsive to various portions of the electromagnetic spectrum, and latent reactive groups that are responsive to ultraviolet, visible or infrared portions of the spectrum are preferred. Latent reactive groups, including those that are described herein, are well known in the art. See, for example, U.S. Pat. No. 5,002,582 (Guire et al., "Preparation of Polymeric Surfaces Via Covalently Attaching Polymers"). The present invention contemplates the use of any suitable latent reactive group for formation of the inventive coatings as described herein.

Photoreactive groups can generate active species such as free radicals and particularly nitrenes, carbenes, and excited states of ketones, upon absorption of electromagnetic energy. Photoreactive groups can be chosen to be responsive to various portions of the electromagnetic spectrum, and that are responsive to the ultraviolet and visible portions of the spectrum are preferred.

Photoreactive aryl ketones are preferred, such as acetophenone, benzophenone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives. Examples of preferred aryl ketones include heterocyclic derivatives of anthrone, including acridone, xanthone, and thioxanthone, and their ring substituted derivatives. Some preferred photoreactive groups are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred latent reactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformnate; sulfonyl azides (—$SO_2$—$N_3$) such as benezensulfonyl azide; and phosphoryl azides [(RO)$_2$PON$_3$] such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetatoacetates (—CO—$CN_2$CO—) such as t-butyl alpha diazoacetoacetate.

Other photoreactive groups include the diazirines (—$CHN_2$) such as 3-trifluoromethyl-3-phenyldiazirine; and ketenes (CH═C═O) such as ketene and diphenylketene.

Peroxy compounds are contemplated as another class of latent reactive groups and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate.

The inventive coating formed on the surface using any suitable method. As described above, a polymer having pendent amine groups and pendent latent reactive groups can be disposed on the surface of an article and the surface can be treated to activate the latent reactive groups thereby bonding the polymer to the surface of the device.

In another method, the polymer is formed on the surface of the device by a graft polymerization method. For example, a monomer including a latent reactive group and a polymerizable group can be disposed and bonded to the surface of the device. A composition of monomers including amine groups can then be disposed on the surface, and a polymerization reaction can be initiated to cause the formation of a polymer chain from and bonded to the surface of the article.

In yet another method, the coating can be formed using a crosslinking agent having two or more latent reactive groups, wherein the crosslinking agent is used to bond the polymer to the surface of the device. The crosslinking agent can have any two or more of the latent reactive groups as described herein. In forming the polymeric coating, the crosslinking agent can be disposed on the surface of the device followed by disposing the polymer having pendent amine groups, or the crosslinking agent can be disposed in combination with the polymer, or both.

If photoreactive groups are present on the cross-linking agent, preferably they are adapted to undergo reversible photolytic homolysis, thereby permitting photoreactive groups that are not consumed in attachment to a polymeric material to revert to an inactive, or "latent" state. These photoreactive groups can be subsequently activated, in order to attach to the polymer with an abstractable hydrogen for covalent bond formation. Thus, excitation of the photo reactive group is reversible and the group can return to a ground state energy level upon removal of the energy source. In some embodiments, preferred cross-linking agents are those groups that can be subject to multiple activations and hence provide increased coating efficiency. In some embodiments the photoreactive moiety is independent of the polymeric material and can be, for example, a crosslinking agent. Exemplary crosslinking agents are described in Applicant's U.S. Pat. No. 5,414,075 (Swan et al.), and U.S. Publication No. 2003/0165613 A1 (Chappa et al.). See also U.S. Pat. No. 5,714,360 (Swan et al.) and U.S. Pat. No. 5,637,460 (Swan et al.).

The non-biodegradable polymer having pendent amine groups can be bonded to a substrate either alone or with other optional components. In its simplest form, the coating composition consists of, for example, (i) a non-biodegradable polymer having a plurality of pendent amine groups and one or more latent reactive groups and/or (ii) a non-biodegradable polymer having a plurality of pendent amine groups and a crosslinking agent having two or more or more latent reactive groups. Other components may be added to the coating composition to change or improve aspects of the coating. The components may be polymeric or non-polymeric components.

Other synthetic or natural, biodegradable or non-biodegradable polymers can be added to the composition to form the coating. A "synthetic polymer" refers to a polymer that is synthetically prepared and that includes non-naturally occurring monomeric units. For example, a synthetic polymer can include non-natural monomeric units such as acrylate, acrylamide, etc. Synthetic polymers are typically formed by traditional polymerization reactions, such as addition, condensation, or free-radical polymerizations. Synthetic polymers can also include those having natural monomeric units, such as naturally-occurring peptide, nucleotide, and saccharide monomeric units in combination with non-natural monomeric units (for example synthetic peptide, nucleotide, and saccharide derivatives). These types of synthetic polymers can be produced by standard synthetic techniques, such as by solid phase synthesis, or recombinantly, when allowed.

A "natural polymer" refers to a polymer that is either naturally, recombinantly, or synthetically prepared and that consists of naturally occurring monomeric units in the polymeric backbone. In some cases, the natural polymer may be modified, processed, dervitized, or otherwise treated to change the chemical and/or physical properties of the natural polymer. In these instances, the term "natural polymer" will be modified to reflect the change to the natural polymer (for example, a "derivitized natural polymer", or a "deglycosylated natural polymer").

Biodegradable materials, such as biodegradable polymers, can also be present in the coating. The biodegradable materials can optionally be present in the same coated layer as the non-biodegradable amine-presenting polymer, can be present in another coated layer, if included in the coating, or both. For example, a coated layer that includes a biodegradable polymer can be formed between the coated layer that includes the non-biodegradable amine-presenting polymer and the article surface, or can be formed on top of the coated layer that includes the non-biodegradable amine-presenting polymer. During culturing, the biodegradable polymer can degrade while the non-biodegradable polymer remains present in the coating and provides an adherent surface during protracted periods of culturing.

In some aspects, polymers that have traditionally been used to form coatings for cell attachment can be included in the coating composition. For example, polypeptide-based polymers such as polylysine, collagen, fibronectin, integrin, and laminin can be included in the coatings. Peptide portions of these polypeptides can also be included in the coating composition. Exemplary binding domain sequences of matrix proteins are shown in Table 1.

TABLE 1

| Fibronectin: | RGDS<br>(SEQ ID NO: 1) | LDV | REDV<br>(SEQ ID NO: 2) |
|---|---|---|---|
| Vitronectin | RGDV<br>(SEQ ID NO: 3) | | |
| Laminin A | LRGDN<br>(SEQ ID NO: 4) | IKVAV<br>(SEQ ID NO: 5) | |
| Laminin B1 | YIGSR<br>(SEQ ID NO: 6) | PDSGR<br>(SEQ ID NO: 7) | |
| Laminin B2 | RNIAEIIKDA<br>(SEQ ID NO: 8) | | |
| Collagen I | RGDT<br>(SEQ ID NO: 9) | DGEA<br>(SEQ ID NO: 10) | GTPGPQGIAGQRGVV<br>(SEQ ID NO: 11) |
| Thrombospondin | RGD | VTXGFYVVMWK<br>(SEQ ID NO: 12) | |

Depending on the reagents present in the coating composition, these polypeptide-based polymers can be in an underivitized or derivitized form. For example, the polypeptide-based polymers can be derivitized with latent reactive groups, and then can be activated along with the latent reactive groups pendent from the non-biodegradable polymer to form the coating. Exemplary combinations can include photo-poly(aminopropylmethacrylamide) or photo-poly(ethyleneimine) with one or more of photo-polylysine, photo-collagen, photo-fibronectin, and photo-laminin, or photo-derivitized portions of polypeptides, including those described herein.

Photoderivatized polypeptides, such as collagen, fibronectin, and laminin can be prepared as described in U.S.

Pat. No. 5,744,515 (Clapper, Method and Implantable Article for Promoting Endothelialization). As described in this patent, a heterobi-functional agent can be used to photoderivatize a protein. The agent includes a benzophenone photoactivatable group on one end (benzoyl benzoic acid, BBA), a spacer in the middle (epsilon aminocaproic acid, EAC), and an amine reactive thermochemical coupling group on the other end (N-oxysuccinimide, NOS). BBA-EAC is synthesized from 4-benzoylbenzoyl chloride and 6-aminocaproic acid. Then the NOS ester of BBA-EAC is synthesized by esterifying the carboxy group of BBA-EAC by carboduimide activation with N-hydroxysuccimide to yield BBA-EAC-NOS. Proteins, such as collagen, fibronectin, laminin, and the like can be obtained from commercial sources.

The protein is photoderivatized by adding the BBA-EAC-NOS crosslinking agent at a ratio of 10-15 moles of BBA-EAC-NOS per mole of protein.

In some aspects, if other optional components are added to the coating composition, it is generally desirable that the non-biodegradable polymer is the primary component in the composition. If the coating includes some biodegradable components, these components may degrade over a period of time, yet leaving the non-biodegradable polymer as the primary component of the coating.

The reagents of the coating composition, such as the polymeric materials, can be prepared in a suitable liquid, such as an aqueous or alcohol-based liquid. For example, the polymeric materials can be dissolved at concentrations in the range of about 0.1 mg/mL to about 50 mg/mL. However, more typically used concentrations are in the range of about 1 mg/mL to about 10 mg/mL.

The coating can be formed by any suitable method including dip coating, in-solution coating, and spray coating.

In the case wherein the coating included photoreactive groups, generally, the step of irradiating can be performed by subjecting the photoreactive groups to actinic radiation in an amount that promotes activation of the photoreactive group and bonding to a target moiety, such as a plastic surface of the cell culture article.

Actinic radiation can be provided by any suitable light source that promotes activation of the photoreactive groups. Preferred light sources (such as those available from Dymax Corp.) provide UV irradiation in the range of 190 nm to 360 nm. A suitable dose of radiation is in the range of from about 0.1 $mW/cm^2$ to about 20 $mW/cm^2$ as measured using a radiometer fitted with a 335 nm band pass filter with a bandwidth of approximately 10 nm.

In some aspects, it may be desirable to use filters in connection with the step of activating the photoreactive groups. The use of filters can be beneficial from the standpoint that they can selectively minimize the amount of radiation of a particular wavelength or wavelengths that are provided to the coating during the activation process. This can be beneficial if one or more components of the coating are sensitive to radiation of a particular wavelength(s), and that may degrade or decompose upon exposure.

Typically, filters are identified by the wavelength of light that is permitted to pass through the filter. Two illustrative types of filters that can be used in connection with the invention are cut-off filters and band pass filters. Generally, cut-off filters are categorized by a cut-off transmittance, at which the light transmittance is approximately 25% of the maximum transmittance. For band pass filters, a range of wavelength is identified for the filter, and the center wavelength is the midpoint of the wavelengths allowed through the filter.

Following the preparation of the coated articles, a washing step can be performed to remove any excess materials that may not be covalently bonded to the surface of the substrate. The coated articles can also be treated to sterilize the articles, by, for example, further UV irradiation.

Some advantages of the present invention are related to the forming a coating that is particularly useful for providing an adherent coating for a wide variety of cell types. Because of the stability of the coating, the coating process can be performed to provide a coated cell culture article, and then the coated article can be delivered to a user or stored for a period of time before use. In other cases, the coating reagents (including at least the non-biodegradable polymer) can be supplied in a kit to a user, who then can perform the coating process on one or more desired articles. Therefore, the invention also provides kits for preparing coatings including a non-biodegradable polymer. The kits can include instructions for forming the coating, and optionally can include methods for culturing cells using articles that are coated with the reagents of the kit.

Generally, the present invention provides coatings and methods for culturing cells using these coatings, wherein the coatings provide an excellent substrate for cell attachment and that can be used in methods wherein the cells can be kept in contact with the coatings for a considerable period of time, such as greater than 14 days, greater than 21 days, greater than 28 days, greater than 35 days, greater than 42 days, greater than 49 days, or greater than 56 days. In some aspects, the cells also may be kept in culture for a time period in the range of about 14 to about 60 days. For example, the cells may be disposed on a coated surface, wherein the cells adhere to the coating and are kept viable in the presence of appropriate media. In some cases the cells may expand by proliferation, but, generally, the phenotype of the cells does not change.

In conjunction with the inventive coating, the cells are typically cultured in a liquid media that is suitable for maintaining cells or promoting the formation of a desired cell type. Various base liquid medias may be used, such as RPMI, which can be supplemented with serum, amino acids, trace elements, hormones, antibiotics, salts, buffers, and growth factors. Factors that can affect aspects of cellular function, including growth and differentiation can also be added to the liquid media. These factors can include neurotrophins, cytokines (such as interleukins), insulin-like growth factors, transforming growth factors, epidermal growth factors, fibroblast growth factors, heparin-binding growth factors, tyrosine kinase receptor ligands, platelet derived and vascular endothelial growth factors, and semaphorins.

Exemplary neurotrophins include nerve growth factor (NGF), neurotrophin, and brain-derived neurotrophic factor; exemplary epidermal growth factors include neuregulin, transforming growth factor a, and netrin; exemplary cytokines include interleukin (IL)-2, IL-3, IL-4, IL-5, IL-6, IL-7, IL-9, IL-11, IL-12, IL-13, IL-15, and G-CSF, leukemia inhibitory factor, ciliary neurotrophic factor (CNTF), cardiotrophin-1, and oncostatin-M; exemplary transforming growth factors include glial-derived neurotrophic factor (GDNF), artemin, neurturin, and persephin.

In some aspects of the invention, the method includes culturing stem cells on the coated substrates as described herein in the presence of appropriate media. Stem cells are multi-potent and plastic, which enables them to be induced to differentiate into various cell types. Stem cells include embryonic stem cells, such those obtained from blastocysts, and adult stem cells, which can be obtained from various tissues in an adult body, such as the bone marrow, which provides a source of hematopoietic stem cells. Embryonic stem cells have essentially unlimited proliferation capacity in vitro and therefore can be expanded greatly for applications, such as those involving tissue regeneration. The coatings of the present invention provide ideal substrates for culturing these cells, as the cells can be maintained and expanded on coated substrates for considerably longer than on other substrates. Therefore, the coatings can greatly facilitate obtaining a great number of stem cells for a desired application such as cell-transplantation or tissue engineering.

Cells cultured according to the processes of the present invention can also be used for drug discovery, gene identification, and for antibody production.

The coatings of the present invention also allow clonal or a small number of cells to be seeded in the coated article vessel, and also allow a longer period before the cells have to be harvested, split, or diluted before a confluent state in culture is reached. The cells can be expanded on any of the two-dimensional or three-dimensional articles described herein.

In some cases, prior to disposing on the coated surface, the cells may be kept on a feeder layer of cells. Following culturing for a period of time on the feeder layer, the cells may be transferred to a cell culture article having the inventive coatings as described herein. According to the invention, it has been discovered that the cells can be cultured for a period of up to about 30 days on the coated substrates without the need to provide a fresh coated surface.

In other aspects of the invention, the invention relates to a method for the differentiation of neural precursors and stem cells. According to the invention, neural precursors can be cultured in the presence of the inventive coatings and one or more factors, such as neurotrophic growth factors, which induce a morphological or biochemical change characteristic of a partial or fully matured neuronal phenotype.

More specifically, in some aspects, the coatings can be used to culture multipotent neuroepithelial stem cells and lineage-restricted intermediate precursor cells which can be induced to differentiate into oligodendrocytes, astrocytes, and neurons. Such precursor cells are present in the CNS at various developmental stages.

In one aspect of the invention, the method is used to promote neurite extension.

PC12 cells (Pheochromocytoma cells), which weakly adhere to plastic, were able to demonstrate excellent adhesion to the coated substrates described herein. Generally PC12 cells are slow growing and can be differentiated with NGF and cAMP acting synergistically. Once differentiated PC12 cells can be maintained for about 14 days. Dexamethasone induces differentiation of a non-neural lineage. Results described herein also show that neural precursor PC12 cells in the presence of the non-biodegradable polymeric amine containing coatings and Nerve Growth Factor (NGF) exhibit neurite extension and the expression of biochemical markers of the sympathetic neuronal phenotypes.

EXAMPLE 1

Photo-Polymeric Reagents

I. Photo-poly(APMA) The preparation of photo-poly(aminopropylmeth-acrylamide) (photo-poly(APMA)/APO2) was carried out by the copolymerization of N-(3-aminopropyl)methacrylamide hydrochloride (APMA-HCl) and N-[3-(4-Benzoylbenzamido)propyl]methacrylamide (BBA-APMA), the preparation of which are described in Examples 2 and 3, respectively, of commonly assigned U.S. Pat. No. 5,858,653.

Copolymerization was carried out by adding to a 2 L flask 2.378 g of BBA-APMA (6.7877 mmol), 0.849 of 2,2'-azobis (2-methyl-propionitrile)(AIBN)(5.1748 mmol), and 0.849 g of N,N,N',N'-tetramethylethylenediamine (TEMED) (6.77 mmol), and then 786 g of dimethylsulfoxide (DMSO) to dissolve the ingredients. The contents were then stirred and deoxygenated with a helium sparge for at least 5 minutes. In a separate flask was dissolved 72.4 g of APMA-HCl (405.215 mmol) in 306 g of DI water with nitrogen sparge. The dissolved APMA-HCl was transferred to the mixture containing BBA-APMA followed by helium sparge for at least 10 minutes. The sealed vessel was then heated overnight at 55° C. to complete the polymerization.

The polymer solution in an amount of 180 mL was then diluted with 180 mL of DI water and dialyzed against deionized water using 12,000-14,000 molecular weight cut-off tubing for at least 96 hours in a 55 gallon tank using a constant flow of 1.25 to 0.35 gallons per minute.

Various coating solutions were prepared with the photo-poly(APMA) polymer ranging from 10 μg/mL to 20 mg/mL in water.

II-IV. Photo-collagen, photo-fibronectin, and photo-laminin Photo-collagen, photo-fibronectin, and photo-laminin were prepared as described in Example 1 of commonly assigned U.S. Pat. No. 5,744,515.

Various photo-laminin coating solutions were prepared ranging from 25 μg/mL to 300 μg/mL in water.

A photo-fibronectin coating solution was prepared at 25 μg/mL in water.

A photo-collagen coating solution was prepared at 25 μg/mL in 0.012 N HCl.

V. Photo-PEI Photo-PEI was prepared by first drying polyethylenimine (PEI; 24.2 wt. % solids; 2000 kg/mol $M_w$; BASF Corp.) under vacuum, and then dissolving 1.09 g of PEI in a 19 mL of 90:10 (v/v) chloroform:methanol solution. The PEI solution was then chilled to 0° C. in an ice bath. In 2.8 mL chloroform was added 62 mg BBA-Cl (4-benzoyl-benzoyl chloride; the preparation of which is described in U.S. Pat. No. 5,858,653) which was allowed to dissolve. The BBA-Cl solution was added to the chilled, stirring PEI solution. The reaction solution was stirred overnight while warming to room temperature (TLC analysis of the reaction solution revealed no unreacted BBA-Cl present after 2.5 hrs.). The next day the reaction solution was transferred into a large flask and one equivalent of concentrated hydrochloric acid was added along with 77.5 mL deionized water. The organic solvents were removed under vacuum at 40° C. until the aqueous PEI solution was clear in appearance. The aqueous PEI solution was then diluted to a final concentration of 5 mg/mL for use as a coating solution.

V. Photo-RGD Photo-RGD was prepared as described in Example 1 of commonly assigned U.S. Pat. No. 6,121,027. A photo-RGD coating solution was prepared at 25 μg/mL in water.

EXAMPLE 2

Substrate Coating

The photo-polymeric reagents prepared in Example 1 of above were coated onto flat (multi-well plates) and three-dimensional substrates (polymeric nanofibers).

In order to coat flat surfaces, coating solutions as described in Example 1 in an amount of 1.0 mL were added to wells of 12 well plates (polystyrene; Corning). For substrate coating the depth of the coating solution (the distance from the surface of the solution to the surface of the substrate, either polystyrene or nanofiber) is generally 5 mm or less, and typically in the range of about 1 or 2 mm. A Dymax™ lamp was used to deliver 200-300 mJ of energy as measured using a 335 nm band pass filter with a 10 nm bandwidth (on average, the wells were irradiated for about 3-4 minutes with the lamp held at a distance of 20 cm from the wells). The wells were then washed with buffered saline pH 7.2 to remove any unbound reagents. The wells were then UV illuminated again to sterilize the wells using the same illumination conditions as described above.

Uncoated 12 well plates were used as controls.

In order to coat three-dimensional surfaces, coating solutions as described in Example 1 in an amount of 0.5 mL were added to disc nanofiber substrates (Synthetic-ECM™, commercially available from Donaldson Co., MN). The substrates were irradiated with the Dymax™ lamp at a distance of about 20 cm for 1 minute. The discs were then washed four times with water. The nanofiber substrates were then UV illuminated again to sterilize the nanofiber substrates.

Uncoated nanofiber substrates were used as controls.

EXAMPLE 3

Attachment Assay of PC12 Cells on Photo-Polymer Coated Substrates

An attachment assay was performed to determine the effects of plating poorly adherent cells (PC12 cells) on various photopolymer substrates. Rat PC12 (pheochromocytoma) cells obtained from ATCC (accession #CRL 1721) were pre-cultured in collagen-coated polystyrene flasks (15 μg/mL, Sigma) in RPMI medium (Invitrogen) containing 10% horse serum, 5% fetal bovine serum, 2 mM Glutamax (Invitrogen), 1 mM sodium pyruvate (Invitrogen), and 10 mM HEPES (Invitrogen). Cells were incubated at 37° C. in 5% $CO_2$/95% air humidified chamber. The media was changed every second day. Cells were trypsinized and passaged when they reached 80% confluency. These culture conditions were followed prior to plating the cells into the 12 well substrates having been coated according to the processes as described in Example 2.

PC12 cells between passage #2 and passage #10 were used for all experiments performed. The cells were trypsinized and seeded at a density of 500,000 cells/well in a 12 well plate in RPMI media at a concentration of 500,000 cells/mL. Cells were incubated in a humidified chamber at 37° C. with 5% $CO_2$ for 48 hours. The cells were at least 99% viable with polygonal morphology prior to plating.

For seeding cells onto nanofibers, the PC12 cells were trypsinized and resuspended in 200 μL of RPMI media. The cell suspension at a density of 500,000 cells/18 mm was carefully added to the coated and uncoated nanofibers (Synthetic-ECM™, product number P609192, commercially available from Donaldson Co., MN) and the cells were allowed to adhere to the nanofibers for 10 minutes at room temperature under the laminar flow hood. After 10 minutes 800 μL of growth media was gently added around the nanofibers and the cells were placed in a humidified, 5% $CO_2$/95% air chamber at 37° C. The media was changed every second day.

MTT Attachment Assay After 48 hours, the growth media was removed and the cells growing on coated and uncoated polystyrene, coated and uncoated nanofibers were washed 4 times with $Ca^{++}$- and $Mg^{++}$-free PBS. These multiple washes removed the loosely bound and unbound cells from the wells. On coated substrates 5% cells were removed by the washes whereas on uncoated substrates 70% were removed by the washes. Cells were then incubated for two hours with MTT in humidified chamber at 37° C. (diluted 1:1 with growth media, Sigma). Media containing MTT was removed and the cells were washed again with PBS to get rid of phenol red. 500 μl of dye solubilizer (a mixture of 0.5 ml of 0.04N HCl/isopropyl alcohol and 0.12 ml of 3% SDS/water) was added and the wells were gently rocked at 30 rpm for 30 minutes (or until the dye completely solubilized) at room temperature. The samples were transferred to a 96 well dish and the absorbance was read at 570 nm in a Spectrophotometer (Spectramax, Molecular Devices).

Results of cell attachment on coated and uncoated flat surfaces (12 well plates) are shown in FIG. 1. The best attachment of the PC12 cells was demonstrated in wells that were coated with photo-poly(APMA) followed by photo-laminin and photo-PEI reagents. Uncoated wells and photo-fibronectin coated substrates were used as controls. PC12 cells express a low level of fibronectin receptors on their surface relative to other cell types that adhere well to fibronectin. (see Tomaselli and Reichardt (1987) *J. Cell Biol.*, 105:2347-2358). The results show that photo-RGD and photo-collagen did not provide coatings that performed as well as photo-poly(AMPA), with approximately a two fold difference in the attachment capacity of photo-poly (AMPA) compared to photo-collagen and photo-laminin.

Figure 2:
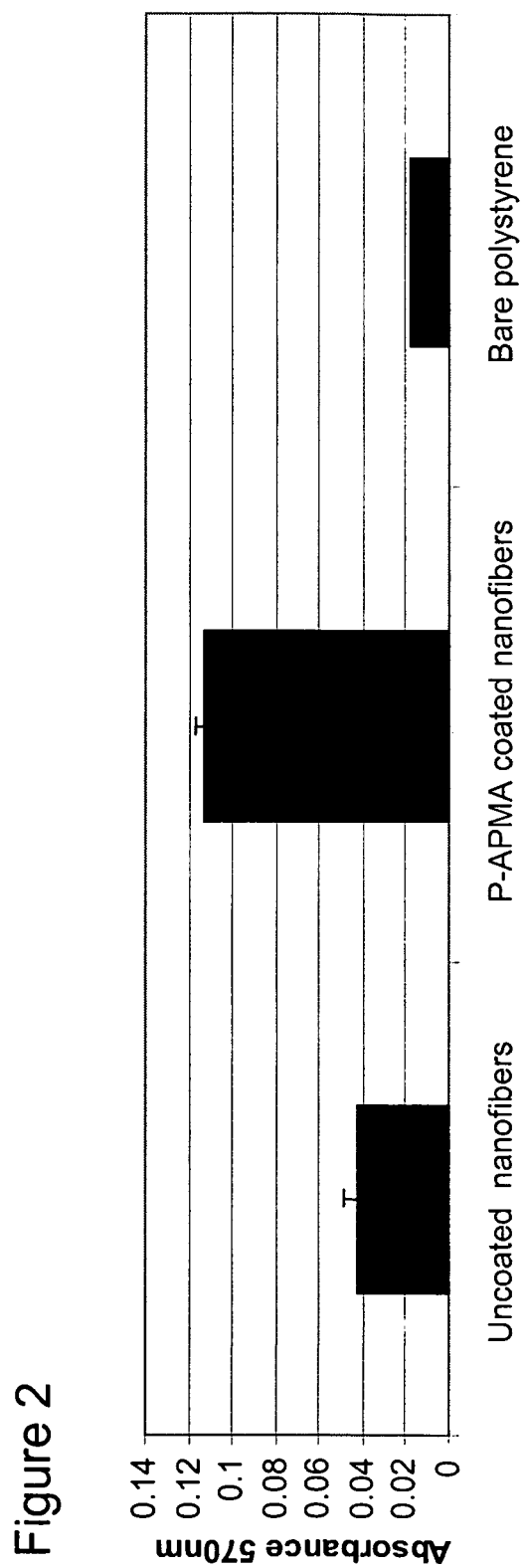
FIG. 2 is a graph showing the results of PC12 cell attachment on photo-polymer coated and uncoated nanofiber substrates.

Results of cell attachment on three dimensional surfaces (nanofibers) are shown in FIG. 2. Similar to results on flat surfaces, the photo-poly(APMA)-coated nanofibers showed firm attachment of weakly anchoring cells as compared to uncoated substrates.

Figure 3:
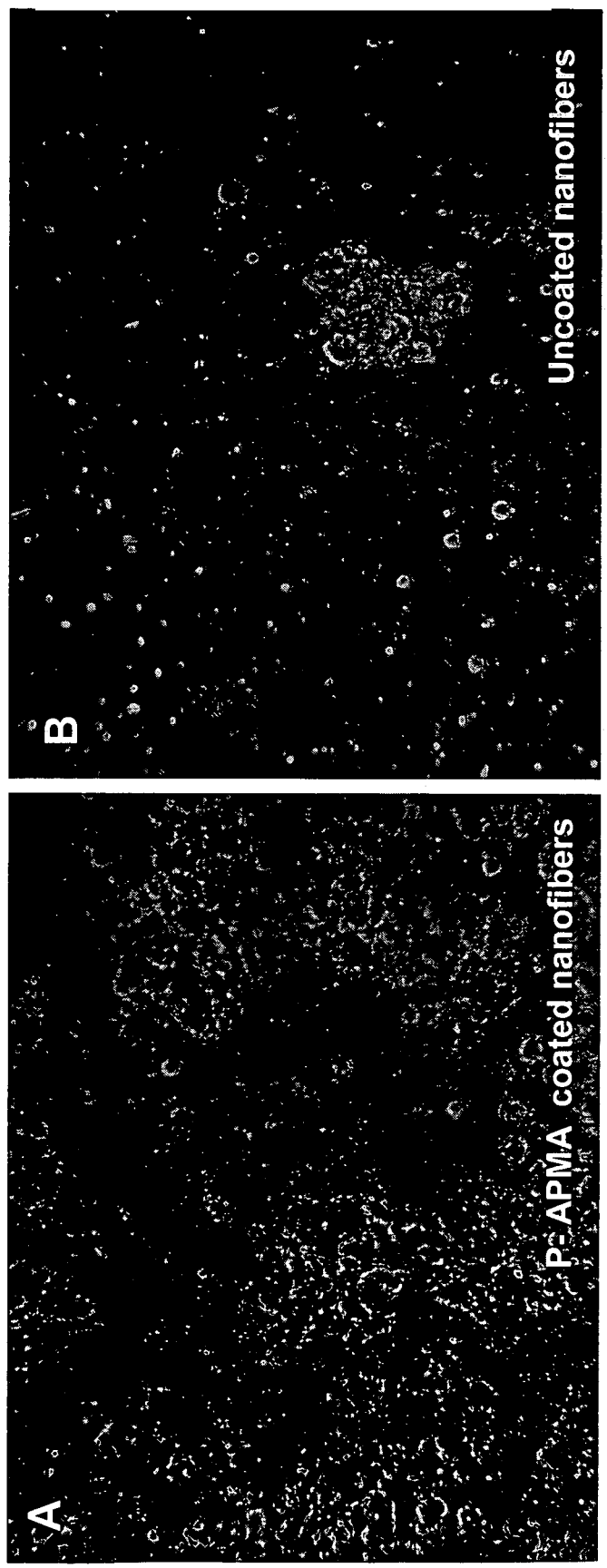
FIG. 3 are bright field microscopic images of PC12 cells growing on photo-poly(APMA)-coated nanofibers (3A) and uncoated nanofibers (3B).

FIG. 3 shows a bright field microscopic image of PC12 cells growing on photo-poly(APMA)-coated nanofibers (3B) and uncoated nanofibers (3A). After 24 hours the picture image was taken. PC12 cells demonstrated good spreading on the photo-poly(APMA)-coated nanofibers, but on the uncoated surfaces the cells attached to each other to form clusters, but were very weakly attached to the uncoated substrate.

Figure 4:
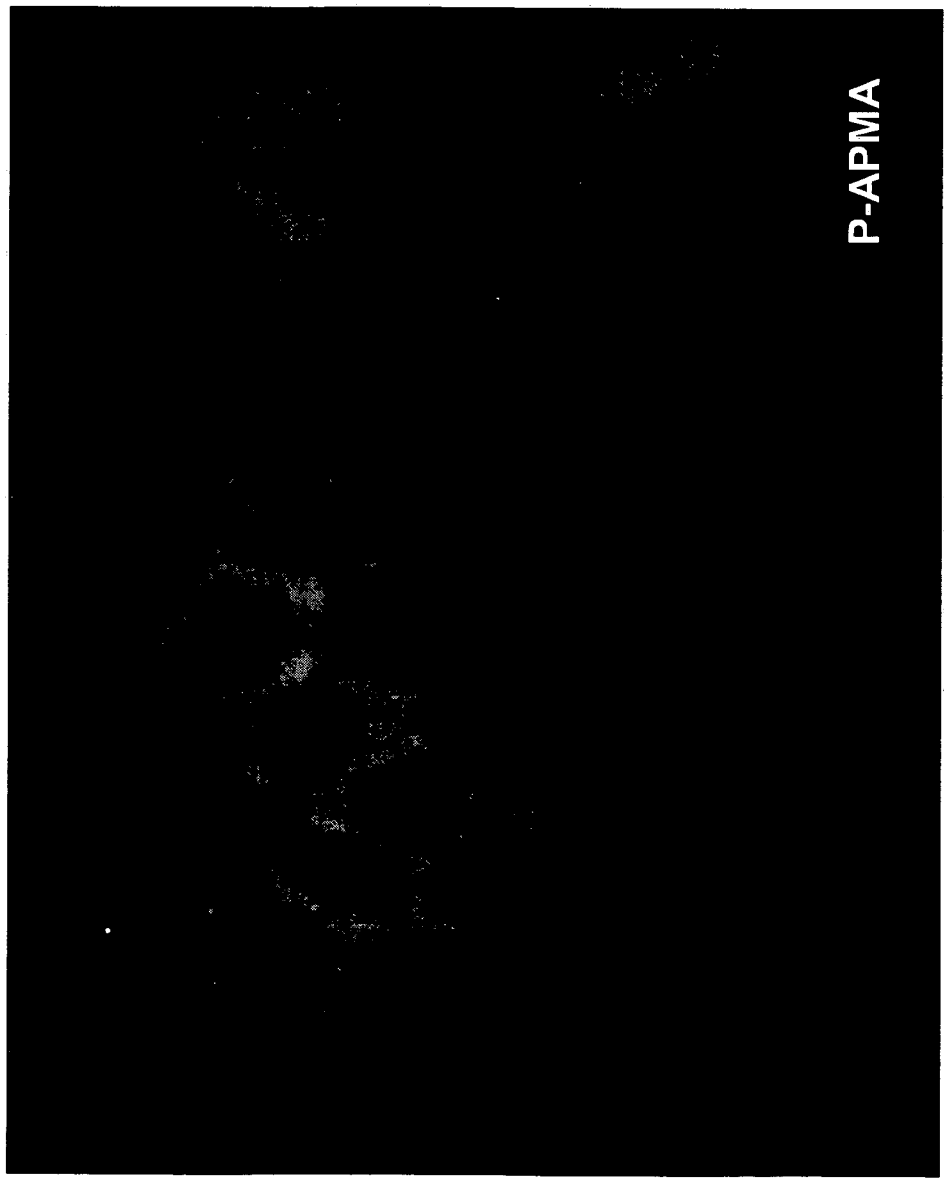
FIG. 4 are fluorescence microscopic images of phalloidin stained PC12 cells having been grown on photo-poly (APMA)-coated nanofibers for a period of 24 hours.

FIG. 4 shows a fluorescence microscopic image of PC12 cells having been grown on photo-poly(APMA)-coated nanofibers for a period of 24 hours and subject to staining with phalloidin (1:500, Molecular Probes). Phalloidin binds to filamentous actin (F-actin) and provides visualization of the cytoskeletal organization of the cells. The staining results show that the PC12 cells cultured on photo-poly (APMA)-coated nanofibers retain their normal polygonal morphology showing the strong binding capacity of the substrate does not affect cell morphology. For phalloidin staining, PC12 cells were fixed with 4% paraformaldehyde for 20 min, washed with 0.1 M PBS three times and incubated for an hour at room temperature with phalloidin conjugated with TRITC diluted in PBS containing 0.5% Triton-X-100™ and 5% goat serum. Cells were washed with 0.1 M PBS and observed under an inverted microscope.

The image shows that actin is organized in a cortical ring instead of being highly spread out, when the cells are cultured on three-dimensional substrates. This organization of actin is observed in either tissues or tissue like matrices (Walpita and Hay (2002) *Nature Rev. Mol. Cell. Biol.*, 3:137-141; U.S. Patent App. No. 2005/0095695A1).

Figure 5:
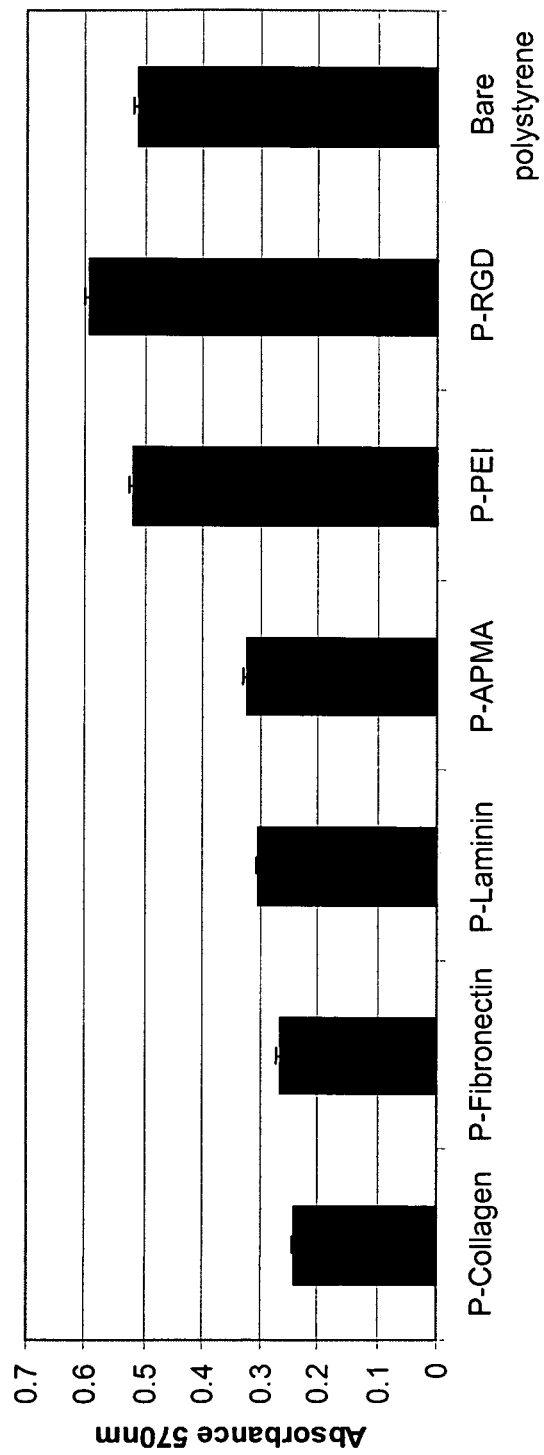
FIG. 5 is a graph showing the results of HFF cell attachment on various photo-polymer coated and uncoated flat surfaces.

To demonstrate the photo-reagents specifically improved the adhesion of a poorly adherent cell line, a strongly adherent cell line was plated on the photo-polymer coated substrates. Human foreskin fibroblasts (HFF) were plated on photo-polymer coated substrates according to the methods used for the PC12 cells and an MTT attachment assay was performed following culturing. FIG. 5 shows that the presence of the photo-reagents generally did not improve the adherence of the HFF cells in comparison to bare polystyrene. No benefits were observed in the attachment of a strongly adherent cell line on various coated substrates tested.

EXAMPLE 4

Proliferation of PC12 Cells on Photo-Polymer Coated Surfaces

PC12 cells were cultured as described in Example 3. BrdU incorporation was tested for cells grown on coated and uncoated nanofibers (Synthetic-ECM™, product number P609186, commercially available from Donaldson Co., MN) and coated and uncoated polystyrene. At day 2, 5-bromodeoxyuridine (BrdU, 1 µM concentration, Sigma) was added to the cultures, which allowed for determination of the number of dividing cells. Cells were pulsed with BrdU for a period of 48 hours and then stained with an anti-BrdU antibody in order to perform immunocytochemistry. PC12 cells were permeabilized by the procedure of S. P Memberg & A. K. Hall ((1995) Neurobiol. 27:26-43). Cell cultures were incubated with the anti-BrdU antibody (1:100, Sigma) in blocking buffer (PBS, 0.5% Triton-X-100™, and 5% goat serum) for a period of one hour, rinsed with PBS and incubated with anti mouse IgG1 secondary antibody (1:200, Southern Biotech) in blocking buffer for an additional hour. Cultures were rinsed three times with PBS and the labeled cells were observed using an inverted microscope (Leica DMLA).

Figure 6:
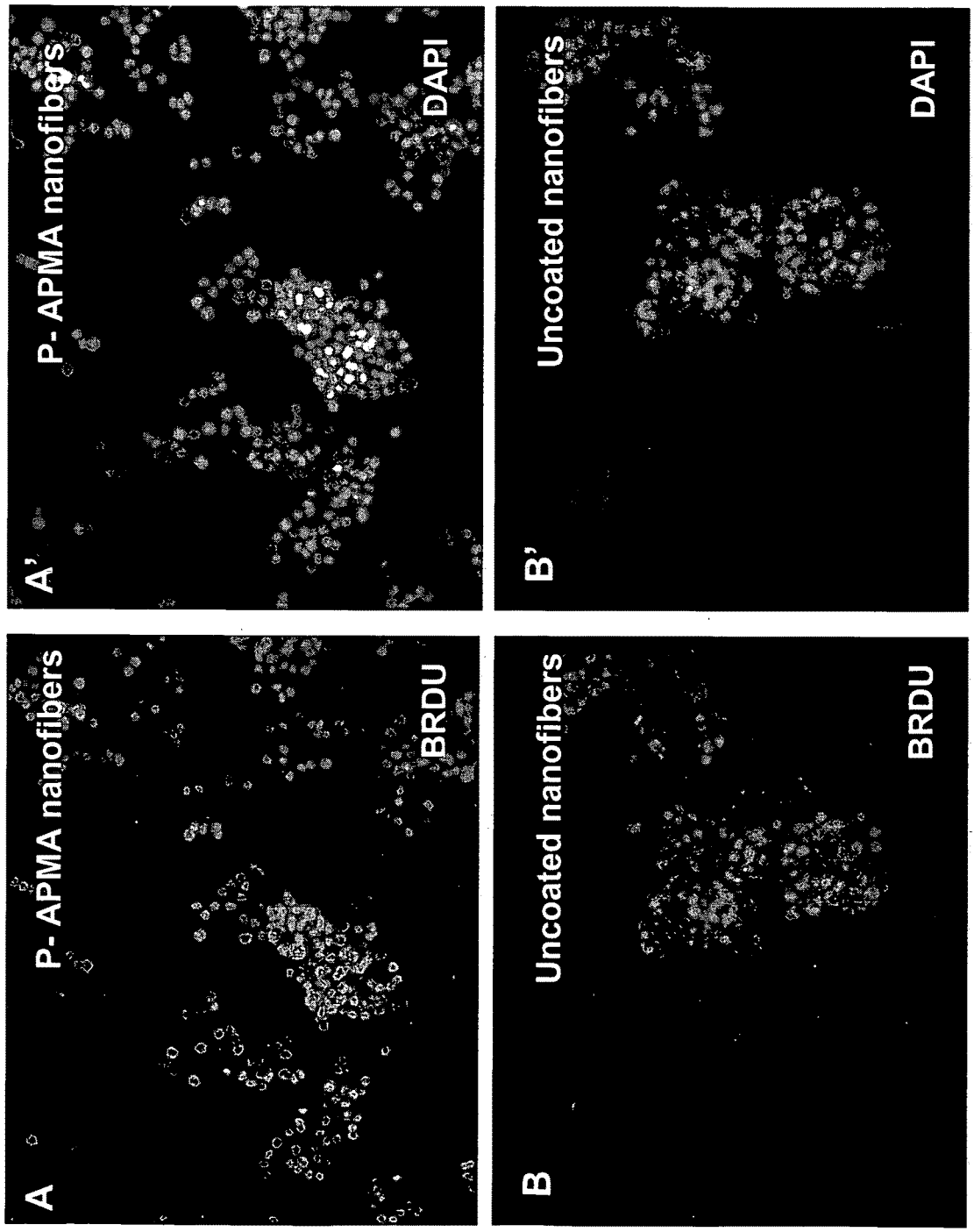
FIG. 6 are fluorescence microscopic images of BrdU incorporation in PC12 cells grown on photo-poly(APMA)-coated nanofibers (A) and uncoated nanofibers (B) and DAPI staining of these cells (A') and (B') respectively.

FIG. 6 shows a fluorescence microscopic image of BrdU incorporation in PC12 cells. The image indicates a greater incorporation of BrdU on photo-poly(APMA)-coated nanofibers as compared to uncoated nanofibers. Greater incorporation of BrdU on photo-poly(APMA)-coated surfaces compared to uncoated surfaces relates to a greater number of dividing cells, and is thought to be due to improved attachment of the cells on the photo-poly(APMA)-coated surfaces. The total number of cells present in a field is indicated by the DAPI staining. Cells grown on the photo-poly(APMA)-coated substrates showed 60% more incorporation of BrdU as compared to photo-polylysine-coated substrates.

EXAMPLE 5

Differentiation of PC12 Cells on Various Coated and Uncoated Surfaces

The differentiation of PC12 cells growing on photo-polymer-coated and uncoated polystyrene 12 well plates, photo-polymer-coated and uncoated nanofibers (Synthetic-ECM™, product number P609186, commercially available from Donaldson Co., MN), PuraMatrix™ (BD Biosciences), and Matrigel™ (BD, Biosciences) was assessed in the presence of NGF (nerve growth factor).

Other photo reagents that were also tested included photo-fibronectin, photo-laminin, photo-collagen, photo-PEI and photo-RGD.

Cells were trypsinized and plated at a density of 30,000 cells/35 mm well in their normal growth media described in Example 3. Twenty four hours later, the growth media was replaced with the differentiation media (RPMI medium (Invitrogen) containing 1% horse serum, 0.5% fetal bovine serum, 2 mM Glutamax (Invitrogen), 1 mM sodium pyruvate (Invitrogen), and 10 mM HEPES (Invitrogen)). Cells were incubated at 37° C. in 5% $CO_2$/95% air humidified chamber and were differentiated for a period of 10 days with the addition of NGF (100 ng/mL, Invitrogen) every second day. To assess differentiation into neurons, the cells were stained for β-III tubulin after 10 days in culture. To perform immunostaining the cells were fixed with 4% paraformaldehyde for 20 min, washed with 0.1 M PBS three times, and then incubated for an hour at room temperature with β-III tubulin primary antibody (1:200, Sigma), in PBS containing 0.5% Triton-X-100™ and 5% goat serum. Cells were washed and incubated with anti mouse secondary antibody (IgG2b, Southern Biotech) for an additional hour. Cells were washed and observed under an inverted microscope to visualize β-III tubulin staining.

Generally, the flat or three-dimensional surfaces that were coated with the photo-polymers produced differentiated cultures enriched in process bearing neurons. The average neurite length on these surfaces was doubled compared to uncoated surfaces. Other photo reagents (photo-laminin, photo-PEI and photo-collagen) were also found to be better than uncoated polystyrene or nanofibers if not better than photo-poly(APMA).

Hence, the photo-poly(APMA) coated surfaces produced better PC12 cell differentiation into neurons compared to uncoated polystyrene, uncoated nanofibers, collagen, PEI and commercially available PuraMatrix™ and Matrigel™ preparations.

Figure 7:
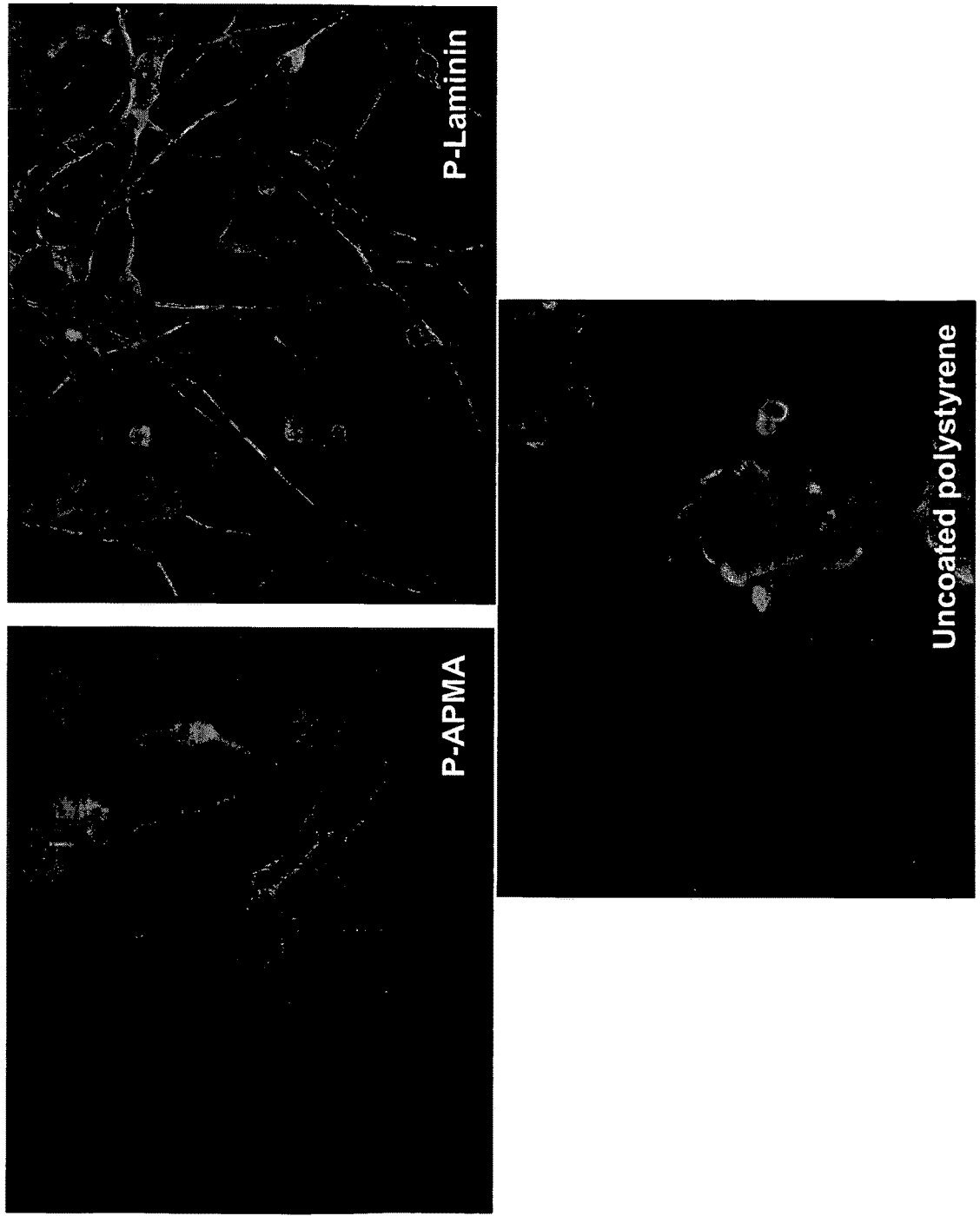
FIG. 7 are fluorescence microscopic images of β-III tubulin-stained PC12 cells grown on various photo-polymer coated and uncoated flat polystyrene surfaces.

FIG. 7 shows that PC12 cells differentiate better on photo-poly(APMA) and photo-laminin coated polystyrene compared to uncoated polystyrene.

Figure 8:
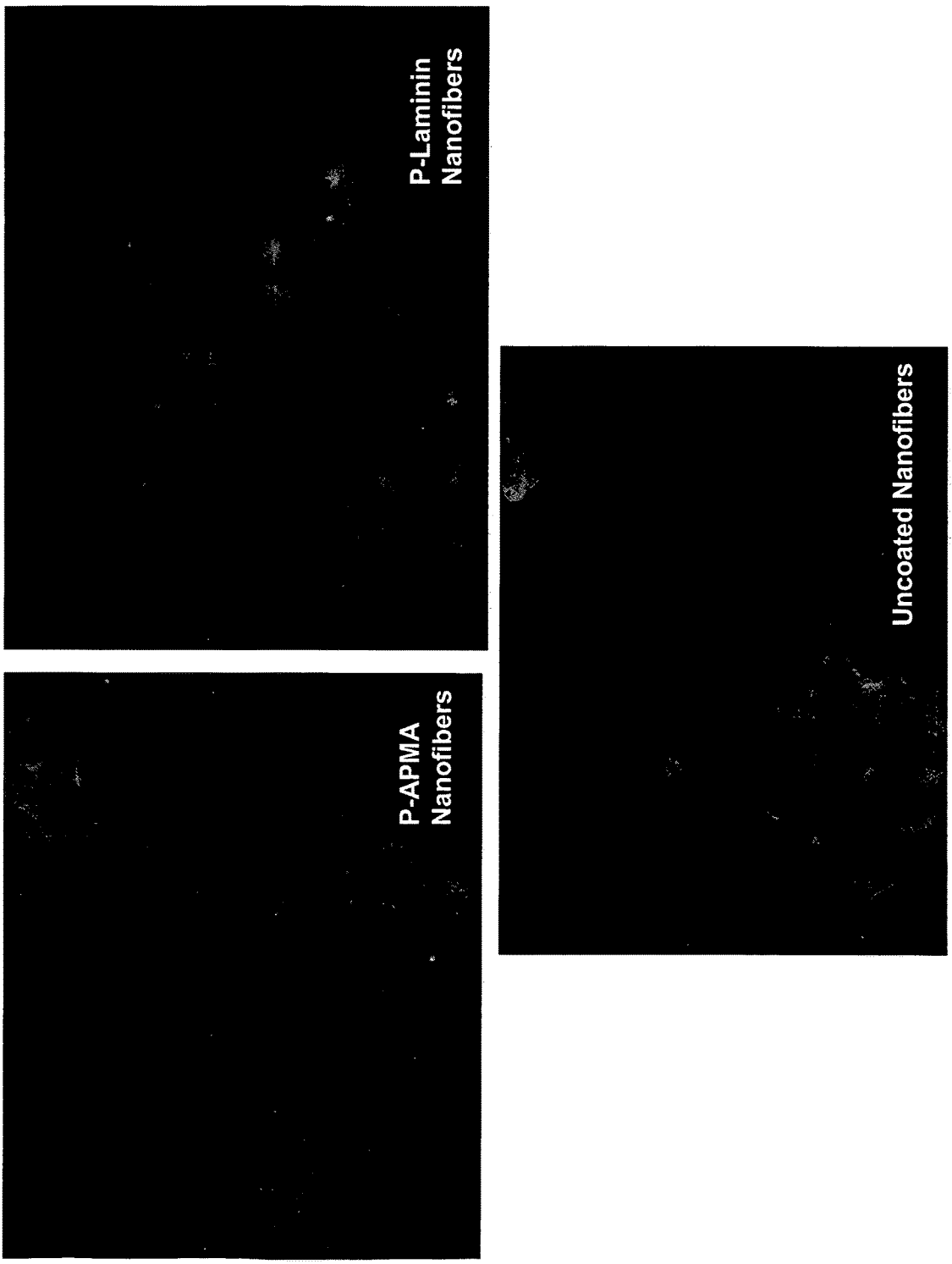
FIG. 8 are fluorescence microscopic images of β-III tubulin-stained PC12 cells grown on various photo-polymer coated and uncoated flat nanofiber surfaces.

FIG. 8 shows that PC12 cells differentiate better on photo-poly(APMA) and photo-laminin coated nanofibers compared to uncoated nanofibers.

Figure 9:
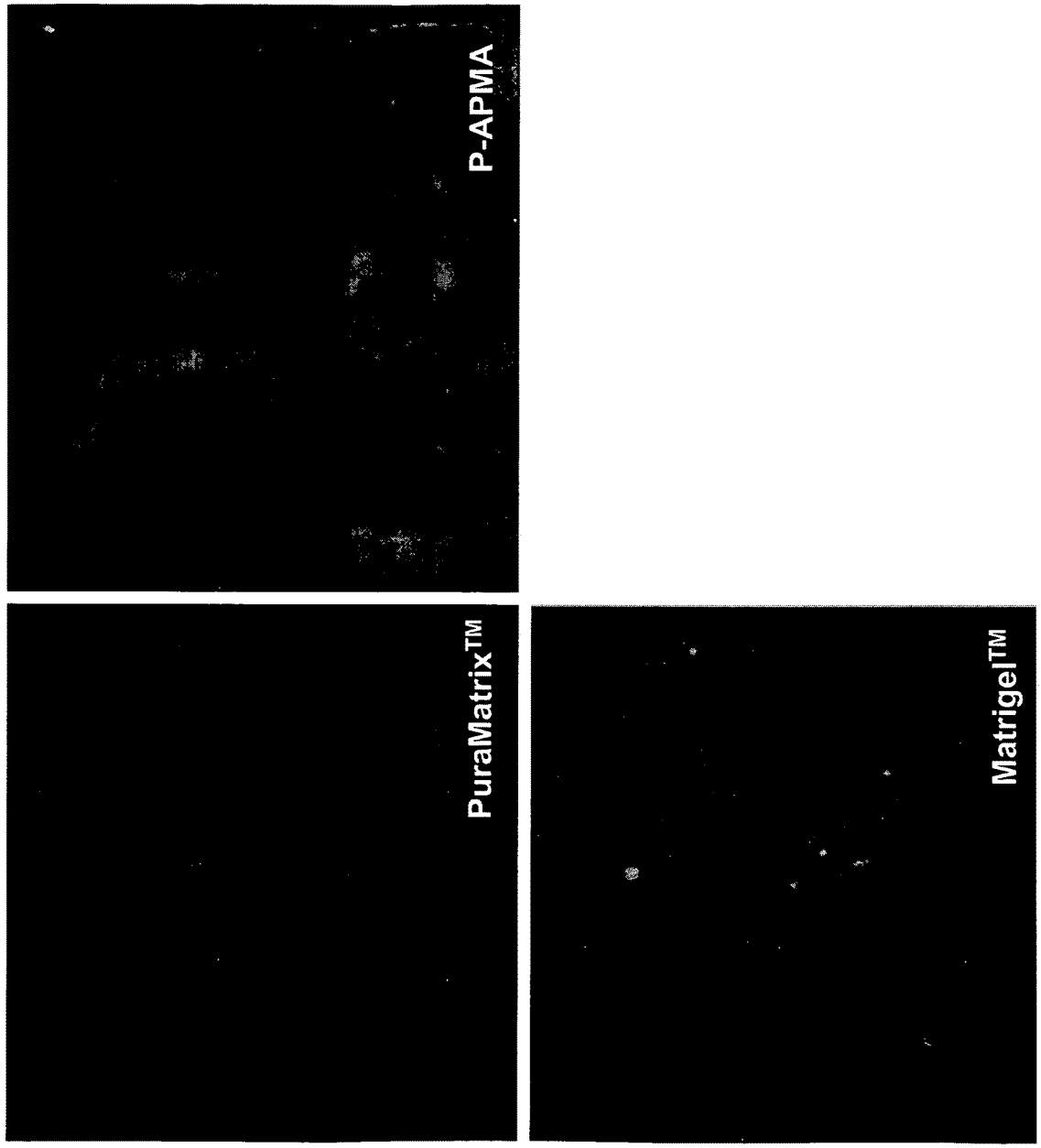
FIG. 9 are fluorescence microscopic images of 0-III tubulin-stained PC12 cells grown on photo-poly(APMA)-coated nanofibers versus other commercially available cell substrates.

FIG. 9 shows that PC12 cells differentiate better on photo-poly(APMA) coated nanofibers compared to PuraMatrix™ and Matrigel™. Photo APMA promoted quantitatively better cell differentiation and longer neurite extension on nanofibers.

Assessments of β-III tubulin staining, neurite morphology, and cell differentiation are summarized in Table 2.

TABLE 2

|  |  | B-III tubulin staining | Neurite morphology | % Differentiation |
|---|---|---|---|---|
| Polystyrene 12-well plates | P-APMA | +++ | ++++ | 60% |
|  | P-PEI | ++ | ++ | 20% |
|  | P-FN | + | + | Less than 5% |
|  | P-Collagen | +++ | +++ | 30% |
|  | P-Laminin | ++++ | ++++ | 80% |
|  | P-RGD | ++ | ++ | 10% |

TABLE 2-continued

|  |  | β-III tubulin staining | Neurite morphology | % Differentiation |
|---|---|---|---|---|
| Uncoated polystyrene 12-well plates |  | + | + | 1% |
| Coated nanofibers | P-APMA | ++++ | ++++ | 50% |
|  | P-PEI | ++ | ++ | 20% |
|  | P-FN | + | + | Less than 5% |
|  | P-Collagen | +++ | +++ | 30% |
|  | P-Laminin | +++ | +++ | 30% |
|  | P-RGD | ++ | ++ | 10% |
| Uncoated nanofibers |  | + | + | 1% |
| PuraMatrix ™ |  | +++ | +++ | 10% |
| Matrigel ™ |  | +++ | ++ | 5% |

++++ very good;
+++ good;
++ fair;
+ poor

EXAMPLE 6

Proliferation of ES-D3 Cells on Photo-Polymer Coated Surfaces

ES-D3 cells from ATCC (Acc. Number CRL-1934) were grown as aggregates in suspension dishes (Nunc) in DMEM-F12 (Invitrogen) with 10% fetal calf serum (FCS, Cambrex) and leukemia inhibitory factor (LIF, 10 ng/ml, Gibco-BRL) for 4 days. The medium was then changed to a chemically defined medium called NEP basal medium (DMEM-F-12 supplemented with 100 µg/ml transferrin, 5 µg/ml insulin, 16 µg/ml putrescine, 20 nM progesterone, 30 nM selenious acid, 1 mg/ml bovine serum albumin, 20 ng/ml bFGF plus B27 and N2 additives and the cells were seeded on fibronectin (15 µg/ml, Sigma) coated polystyrene dishes, photo poly(APMA)-coated and uncoated nanofibers (Synthetic-ECM™, product number P610304, commercially available from Donaldson Co., MN). Medium was changed every 2 days and the cells were maintained at 37° C. in 5% $CO_2$/95% air humidified chamber (Mujtaba and Rao (1999) *Developmental Biology* 214:113-127).
Photo-poly(APMA)-coated surfaces were used with the ES-D3 cells Nestin Staining for proliferating ES-D3 cells.

The ES-D3 cells were assayed at 24 hours and 48 hours. ES-D3 cells were stained for the presence of nestin, a marker for undifferentiated stem cells (U. Lendahl et al. (1990) *Cell* 60:585-95) as follows. Cells were fixed for 20 mm at room temperature with 4% paraformaldehyde. They were washed three times with 0.1 M PBS, pH 7.4 and incubated with primary antibody to rat nestin (rat 401, DSHB) diluted 1:1 diluted in PBS containing 0.5% Triton-X-100™ and 5% goat serum for two hours at room temperature. Cells were then washed for 5 min with 0.1M PBS and incubated with anti mouse secondary (1:200, Southern Biotech) diluted in PBS containing 0.5% Triton-X-100™ and 5% goat serum for an additional hour after which they were washed three times with 0.1 M PBS and observed under an inverted microscope (Leica, DMLA). Nestin was double labeled with BrdU and the double labeling experiments were performed by simultaneously incubating cells in appropriate combinations of primary antibodies followed by non-cross reactive secondary antibodies.

Figure 10:
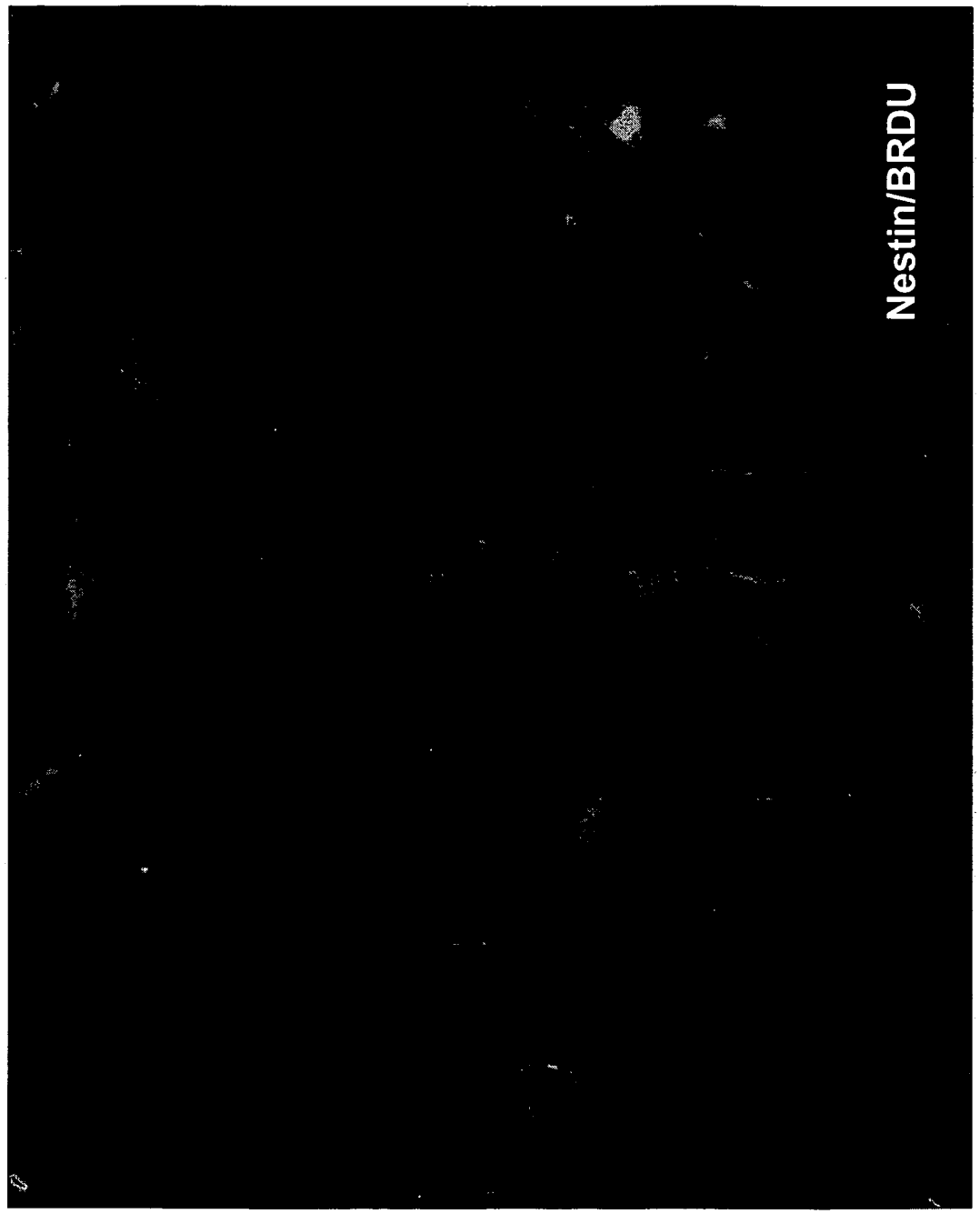
FIG. 10 is a fluorescence microscopic image of nestin/BrdU stained ES-D3 cells grown on photo-poly(APMA)-coated nanofibers.

FIG. 10 shows the presence of nestin/BrdU positive ES-D3 cells on coated nanofibers. The majority of the cells are nestin positive and negative for all other lineage markers tested (GFAP, β-III tubulin, and O4) which indicates that cultures of undifferentiated stem cells can be maintained on these totally synthetic surfaces coated with photo-poly (APMA).

EXAMPLE 7

Differentiation of ES-D3 Cells on Coated Surfaces

Nestin positive ES-D3 cells growing on photo-poly (APMA) coated nanofibers (Synthetic-ECM™, product number P609192, commercially available from Donaldson Co., MN) in basal medium (DMEM-F-12 supplemented with 100 µg/ml transferrin, 5 µg/ml insulin, 16 µg/ml putrescine, 20 nM progesterone, 30 nM selenious acid, 1 mg/ml bovine serum albumin, 20 ng/ml bFGF plus B27 and N2 additives). Cells were induced to differentiate by removal of bFGF from the growth medium and addition of either retinoic acid (1 µM, Sigma), PDGF BB (10 ng/ml, Sigma), CNTF (10 ng/ml, Sigma), 10% serum (FBS, Invitrogen) (Mujtaba and Rao, ibid.). After six days in culture with the daily addition of inducing agents the stem cells differentiated into neurons, oligodendrocytes and astrocytes. The differentiation was achieved without changing the substrate of the cells.

β-III Tubulin Staining

The cells were fixed with 4% paraformaldehyde for 20 min, washed with 0.1 M PBS three times and incubated for an hour at room temperature with β-III tubulin (1:200, Sigma), a marker for neurons in PBS containing 0.5% Triton-X-100™ and 5% goat serum. Cells were washed and incubated with anti mouse secondary antibody (IgG2b, Southern Biotech) for an additional hour. Cells were washed and observed under an inverted microscope.

In some instances we also stained with DAPI as follows. Cells prepared as above were washed with DAPI solution (diluted 1:1000 in 100% MeOH, Boehringer Mannheim). Fixed cells were incubated with DAPI solution for 15 min at room temperature.

O4 Staining for Oligodendrocytes

Cells were fixed for 10 min at room temperature with 4% paraformaldehyde. Cells were washed three times for 5 min with 0.1 M PBS, pH 7.4. Cells were incubated with primary antibodies to 04 (6 µg/ml, Chemicon) in medium containing 5% BSA for two hours at room temperature. Preparations were then washed three times for 5 min with 0.1 M PBS, pH 7.4. Cells were incubated with secondary antibodies, and further processed as described above for β-III tubulin.

GFAP Staining for Astrocytes

Cells were fixed for 20 min at room temperature with 4% paraformaldehyde. Cells were washed three times with 0.1 M PBS, pH 7.4. Cells were incubated with primary antibody to GFAP (1:500, Chemicon) in PBS containing 0.5% Triton-X-100™ and 5% goat serum for two hours at room temperature. Cells were washed and incubated with anti mouse secondary antibody and further processed as described above for β-III tubulin.

Uncoated nanofibers and polystyrene, double coated with poly-lysine (15 ug/ml, Sigma) and laminin (15 ug/ml, Gibco BRL), were used as controls.

Better differentiation into appropriate cell types is achieved on coated nanofibers compared to uncoated nanofibers and tissue culture plastic double coated with poly-lysine/laminin, and that this differentiation is achieved by the mere addition of appropriate inducing agents to the same substrate.

Figure 11:
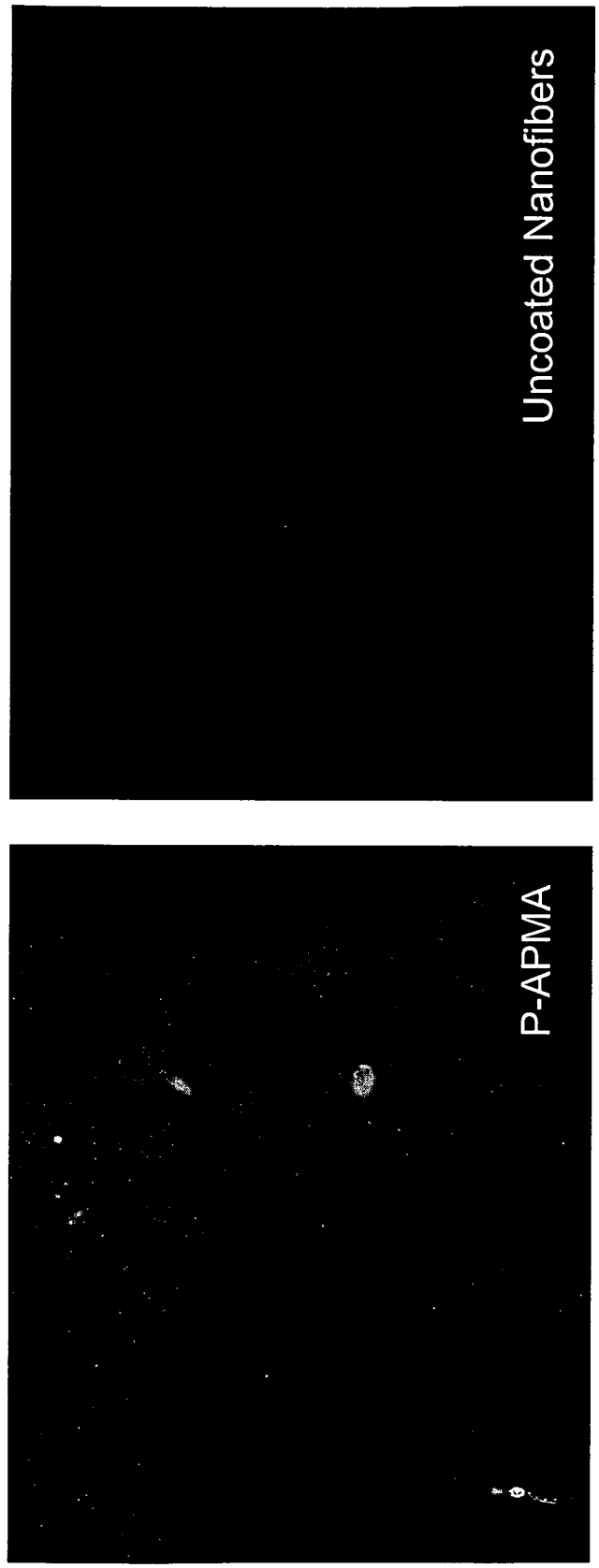
FIG. 11 are fluorescence microscopic images demonstrating neurite morphology of beta III tubulin-stained ES-D3 grown on photo-poly(APMA)-coated nanofibers and uncoated nanofibers. The image shows that ES-D3 cells differentiate into process bearing neurons with longer neurite lengths compared to neurons growing on uncoated nanofibers where the processes are short and stubby.

FIG. 11 shows that ES-D3 cells differentiate into process bearing neurons with longer neurite lengths compared to neurons growing on uncoated nanofibers where the processes are short and stubby.

Figure 12:
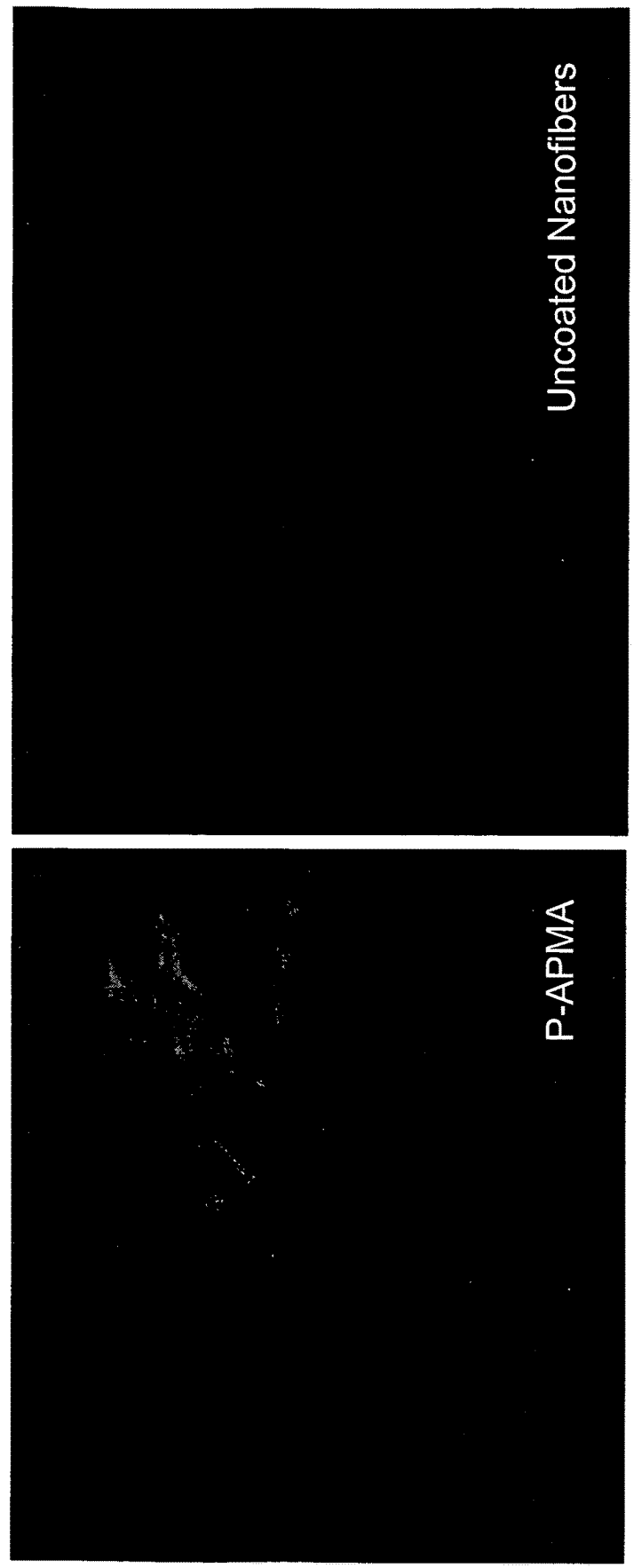
FIG. 12 are fluorescence microscopic images of GFAP-stained ES-D3 grown on photo-poly(APMA)-coated nanofibers and uncoated nanofibers.

FIG. 12 shows that ES-D3 cells differentiate into Type I and Type II GFAP positive astrocytes on photo-poly (APMA) coated nanofibers. Note that the cells are much brighter on coated nanofibers.

EXAMPLE 8

Growth of PC12 Cells at Clonal Density

PC12 cells were plated at a density of 300 cells/32 mm nanofiber disc (Synthetic-ECM™, product number P609186, commercially available from Donaldson Co., MN) placed in a 35 mm well and were differentiated for a period of 30 days with the addition of NGF every second day (as described in Example 5). After 30 days, the cells were fixed with 4% paraformaldehyde for 20 min, washed with 0.1 M PBS three times and incubated for an hour at room temperature with β-III tubulin (1:200, Sigma) in PBS containing 0.5% Triton-X-100™ and 5% goat serum. Cells were washed and incubated with anti mouse secondary antibody (IgG2b, Southern Biotech) for an additional hour. Cells were washed and observed under an inverted microscope. Single cells started to form clones after four days in culture. The clones grew rapidly and remained firmly attached to the coated surfaces.

EXAMPLE 9

Lone Term Cultures of PC12 Cells on Photo-Polymer Coating

Figure 13:
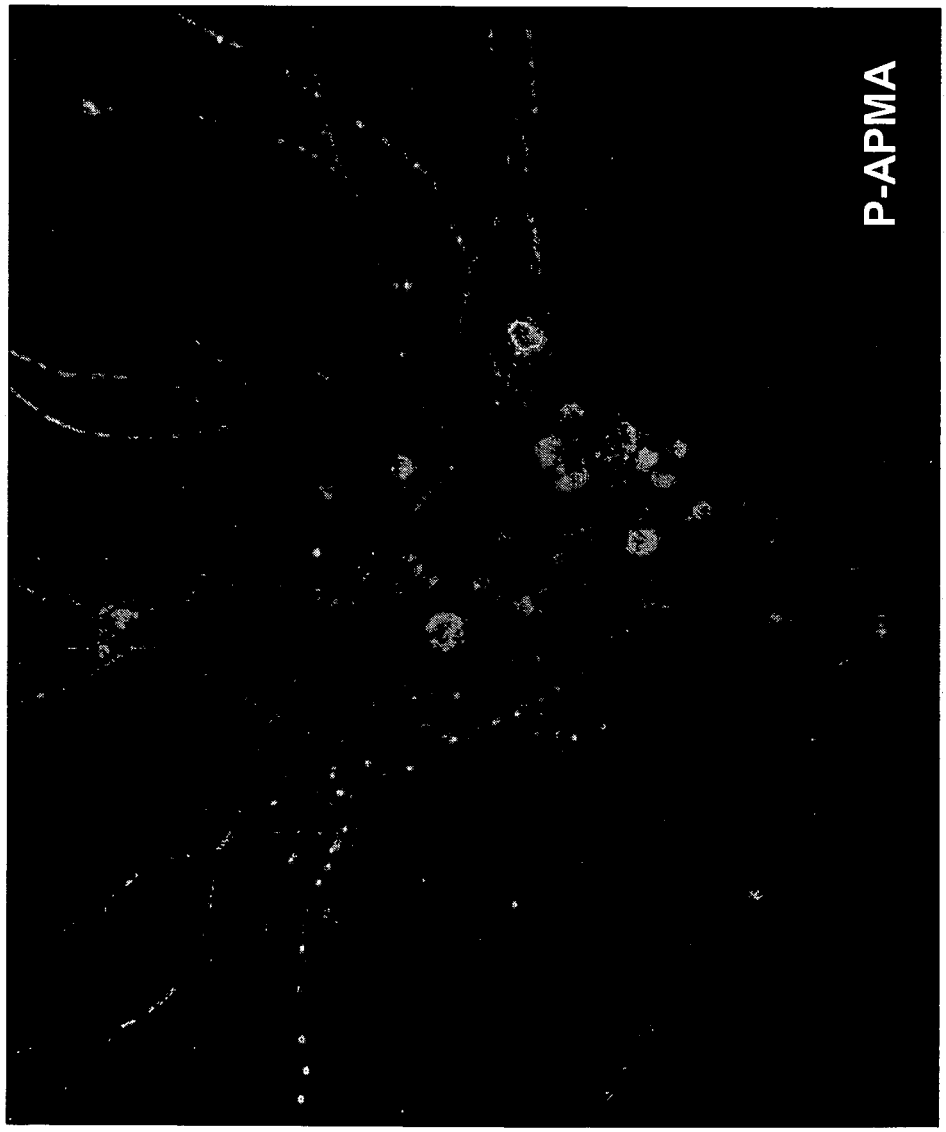
FIG. 13 is a fluorescence microscopic image demonstrating extensive neurite morphology of β-III tubulin-stained PC12 cells grown on photo-poly(APMA)-coated nanofibers and differentiated for a period of 30 days.

PC12 cells cultured as described in Example 8 were maintained for a period of 45 days and processed for β-III tubulin. FIG. 13 shows differentiated PC12 cells growing on photo-poly(APMA)-coated surfaces. After 30 days in culture, the cells were robust and displayed extensive neurites.

What is claimed is:

1. A medical article comprising: a body member configured for insertion into the vasculature of a patient; and a surface coating on at least a portion of the body member of the medical article, the surface coating comprising a copolymer having pendent group-containing first and second monomeric units, wherein the pendent-group containing first monomeric unit has a pendent amine-containing group and is selected from the group consisting of

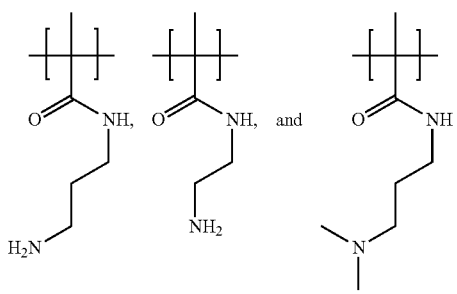

and is present in the copolymer in an amount in the range of 90-99.95% mol.; and the second monomeric unit is:

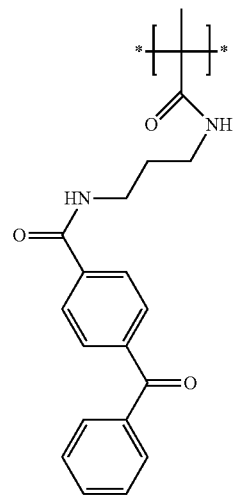

and is present in the copolymer in an amount in the range of 0.05-10% mol., wherein the pendent group-containing first and second monomeric units total 100% of all monomeric units in the copolymer.

2. A medical article comprising a catheter, a surface coating formed on at least a portion of the medical article, the medical article comprising a material selected from the group consisting of polyesters, polypropylenes, polyethylenes, polyurethanes, polytetrafluoroethylenes, polyamids, polyethylene terephthalate (PET), nylon, and velour, the surface coating comprising a composition comprising a copolymer having pendent group-containing first and second monomeric units, wherein the pendent group-containing first monomeric unit has a pendent-amine containing group and is selected from the group consisting of

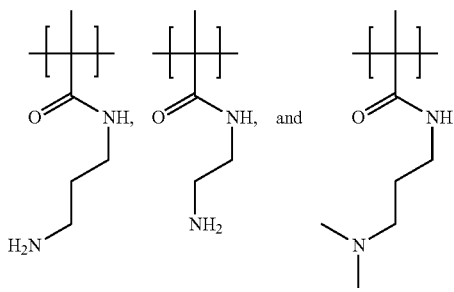

and is present in the copolymer in an amount in the range of 90-99.95% mol.; and
the second monomeric unit is:

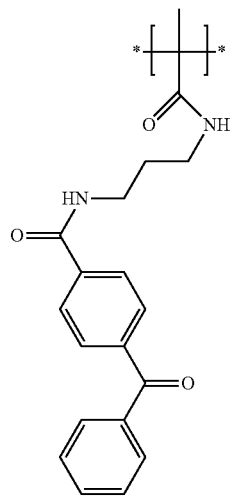

and is present in the copolymer in an amount in the range of 0.05-10% mol., wherein the pendent-group containing first and second monomeric units total 100% of all pendent group monomeric units in the copolymer.

3. A coated medical article comprising:
(a) a medical article selected from the group consisting of a vascular implant, a vascular graft, a vascular prosthesis, an endoprosthesis, a stent-graft, are endovascular-stent combination, a small diameter graft, an abdominal aortic aneurysm graft, a wound dressing, a mesh with hernia plug, a uterine bleeding patch, an atrial septic defect (ASD) patch, a patent foramen ovale (PFO) patch, a ventricular septal defect (VSD) patch, an atrial septic defect closure, patent foramen ovale closure, and ventricular septal defect closure, a left atrial appendage filter, a central venous access catheter, a vascular access catheter, an abscess drainage catheter, a drug delivery catheter, a parental feeding catheter, an intravenous catheter, a stroke therapy catheter, a blood pressure and stent graft catheter, an anastomotic closure, an aneurysm exclusion device, a glucose sensor, a birth control device, a breast implant, a cardiac sensor, a cerebral spinal fluid (CSF) shunt, a glaucoma drain shunt, an ear drainage tube, a hympanostomy vent tub, an implanted drug infusion tube cuff, a catheter cuff, a neurological catheters, a neuropatch, and an orthopedic joint implant; and
(b) a surface coating on at least a portion of the medical article, the surface coating comprising a copolymer formed from a composition having a pendent-group containing first monomer and a second monomer, wherein the pendent-group containing first monomer is present in the composition in an amount in the range of 90-99.95% mol. of total monomers, the second monomer is present in the composition in an amount in the range of 0.05-10% mol. of total monomers, and the pendent-group containing first monomer and second monomer constitute 100% mol. of total monomers in the composition, wherein the pendent group-containing first monomer has a pendent-amine-containing group and is selected from the group consisting of 3-aminopropylmethacrylamide, 3-aminoethylmethacrylamide, dimethylaminopropylmethacrylamide, and salts thereof, and the second monomer comprises N-[3-(4-benzoylbenzamido)propyl]methacrylamide.

4. The medical article of claim 3 wherein the first monomer provides a positive charge to the coating at a pH in the range of 6-8.

5. The medical article of claim 3 wherein the copolymer has a molecular weight in the range of 20 kDa to 2000 kDa.

6. The medical article of claim 3 wherein the coating is present on a vascular prosthesis.

* * * * *